US012246055B2

(12) United States Patent
Tiberg et al.

(10) Patent No.: US 12,246,055 B2
(45) Date of Patent: Mar. 11, 2025

(54) LIPID-CONTROLLED RELEASE COMPOSITIONS

(71) Applicant: CAMURUS AB, Lund (SE)

(72) Inventors: Fredrik Tiberg, Lund (SE); Catalin Nistor, Lund (SE); Markus Johnsson, Lund (SE); David Hemmerlin, Basel (CH); Johannes Kluge, Basel (CH); Priyanga Wickramanayake, Basel (CH)

(73) Assignee: CAMURUS AB (SE)

( * ) Notice: Subject to any disclaimer, the term of this patent is extended or adjusted under 35 U.S.C. 154(b) by 584 days.

(21) Appl. No.: 17/606,864

(22) PCT Filed: May 29, 2020

(86) PCT No.: PCT/EP2020/065073
§ 371 (c)(1),
(2) Date: Oct. 27, 2021

(87) PCT Pub. No.: WO2020/240017
PCT Pub. Date: Dec. 3, 2020

(65) Prior Publication Data
US 2022/0202898 A1 Jun. 30, 2022

(30) Foreign Application Priority Data
May 29, 2019 (SE) .................... 1950645-0

(51) Int. Cl.
| | | |
|---|---|---|
| A61K 38/00 | (2006.01) | |
| A61K 38/12 | (2006.01) | |
| A61K 47/10 | (2017.01) | |
| A61K 47/24 | (2006.01) | |
| A61M 5/28 | (2006.01) | |
| A61M 5/31 | (2006.01) | |
| A61M 5/315 | (2006.01) | |
| A61J 1/06 | (2006.01) | |

(52) U.S. Cl.
CPC .............. *A61K 38/12* (2013.01); *A61K 38/00* (2013.01); *A61K 47/10* (2013.01); *A61K 47/24* (2013.01); *A61M 5/31513* (2013.01); *A61J 1/065* (2013.01); *A61M 2205/0222* (2013.01)

(58) Field of Classification Search
CPC ........ A61K 38/00; A61K 38/08; A61K 38/10; A61K 38/12; A61K 38/31; A61M 5/3131; A61M 5/31513; A61M 2205/0222; A61J 1/065
See application file for complete search history.

(56) References Cited

U.S. PATENT DOCUMENTS

| | | | |
|---|---|---|---|
| 2007/0148745 A1* | 6/2007 | Oi Ming .............. | C12P 7/6418 435/158 |
| 2021/0146054 A1* | 5/2021 | Cully .................... | A61M 5/20 |
| 2021/0169965 A1* | 6/2021 | Dey ...................... | A61K 47/22 |

FOREIGN PATENT DOCUMENTS

| | | |
|---|---|---|
| JP | 2014169244 A | 9/2014 |
| WO | 2006131730 A1 | 12/2006 |
| WO | 2012/160213 A1 | 11/2012 |

OTHER PUBLICATIONS

Demeule et al., The AAPS Journal 2010, 12 (4), 708-715.
Gerhardt et al., Journal of Pharmaceutical Sciences 2014, 103, 1601-1612.
Demeule et al., "Characterization of Particles in Protein Solutions: Reaching the Limits of Current Technologies", The AAPS Journal, 12(4): 708-715 (2010).
Gerhardt et al., "Protein aggregation and particle formation in prefilled glass syringes", Journal of Pharmaceutical Sciences, 103(6): 1601-1612 (2014).
International Preliminary Report on Patentability in International Application No. PCT/EP2020/065073, dated Nov. 16, 2021.
International Search Report in International Application No. PCT/EP2020/065073, dated Aug. 21, 2020.
Hou et al., "Discussion on Insoluble Particles of Protein Drugs Caused by Silicone Oil in Prefilled Syringes," Chinese Journal of Pharmaceuticals 2018, 49, 6, 730-736.

\* cited by examiner

*Primary Examiner* — Jeffrey E. Russel
(74) *Attorney, Agent, or Firm* — RAPHAEL BELLUM PLLC

(57) ABSTRACT

The disclosure provides a glass syringe or a glass cartridge, for parenterally administering, containing a lipid-based pre-formulation suitable for refrigerated storage, wherein the lipid-based pre-formulation includes 20-80 wt % of a diacyl glycerol having a fatty acid composition of at least 98% oleic acid (18:1), as determined in accordance with method C, 2.4.22 (Composition of fatty acids by gas chromatography), European Pharmacopoeia 9.0; 20-80 wt % of a phospholipid; 1-30 wt % of a solvent; and a bioactive agent.

23 Claims, 5 Drawing Sheets

LIPID-CONTROLLED RELEASE COMPOSITIONS

FIELD

The present disclosure relates to lipid compositions, particularly those suitable for use in formulations of medicaments, and to pre-formulations comprising such lipid compositions. The disclosure additionally relates to the use of certain lipid compositions in preventing or reducing the formation of long-lived precipitates during storage of lipid medicaments.

BACKGROUND TO THE DISCLOSURE

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable or necessary, since self-administration may be difficult and thus cause inconvenience and/or poor compliance. In such cases it would be advantageous for a single administration to provide active agent at a therapeutic level over the whole period during which activity is needed.

Some patients undergoing treatment will typically require a therapeutic dose to be maintained for a considerable period and/or ongoing treatment for many months or years. Thus a depot system allowing loading and controlled release of a larger dose over a longer period would offer a considerable advantage over conventional delivery systems.

Certain of the formulations of the present disclosure generate a non-lamellar liquid crystalline phase following administration. The use of non-lamellar phase structures (such as liquid crystalline phases) in the delivery of bioactive agents is now relatively well established. A highly effective lipid depot system is described in WO2005/117830. However, there remains scope for achieving depot formulations having improved performance in some respects.

In particular, it has been observed that when certain lipid-based compositions, such as the lipid depot systems described in WO2005/117830, are returned to room temperature after having been stored under refrigerated conditions, a cloudy or "turbid" appearance may remain. This turbidity remains even when the pre-formulations are left to equilibrate at room temperature. Turbidity is undesirable in injectable medicaments and may be prohibited for regulatory and/or safety reasons. As used herein "turbidity" is used to indicate a lack of clarity in a solution. This may be due to a suspension of a liquid or solid material in the solution, a precipitation, separation or other cause.

Turbidity, including opalescence and formation of precipitates in a medicament (which take a long time to re-dissolve, or remain insoluble) can mean that the medicaments are more difficult to administer to a subject or in many cases would be prohibited from such administration. Since some active agents must be stored under refrigerated conditions in order to prevent degradation of that active agent, the formation of these long-lived precipitates and/or turbidity have the potential to limit the choice of active agents that can, in practice, be administered as part of such lipid-based formulations.

There therefore exists a need to provide a way of preparing lipid-based formulations which have been subjected to storage under refrigerated conditions and can be safely administered to a subject, free from turbidity, opalescence and/or precipitates.

The inventors have now established that lipid-based formulations having reduced turbidity and/or precipitate formation after storage under refrigerated conditions can be provided by preparing the formulations using a high-purity diacyl glycerol composition (at manufacturing scale) in combination with particular glass syringes having an inner surface in contact with lipid-based formulations and free of silicone oil, or even free of a pre-applied lubricant. By preparing lipid-based formulations comprising a high-purity diacyl glycerol composition, such as glycerol dioleate, and filling in glass syringes free of silicone oil, the formation of precipitates and opalescence/turbidity after storage under refrigerated conditions and subsequent equilibration at room temperature is surprisingly reduced, while the injectability is maintained.

SUMMARY

In a first aspect, the present disclosure provides a glass syringe or a glass cartridge, containing a lipid-based pre-formulation, wherein at least the inner surface of the glass syringe or glass cartridge is in contact with the lipid-based pre-formulation and said inner surface is free of pre-applied silicone lubricant, and wherein the lipid-based pre-formulation comprises
  a) 20-80 wt % of a diacyl glycerol having a fatty acid composition of at least 98% oleic acid (18:1), as determined in accordance with method C, 2.4.22 (Composition of fatty acids by gas chromatography), European Pharmacopoeia 9.0;
  b) 20-80 wt % of a phospholipid;
  c) 1-30 wt % of a solvent;
  d) a bioactive agent;
  wherein a) and b) is at least 94 wt % of the total lipid content of the lipid-based pre-formulation, and the lipid-based pre-formulation is a clear liquid having a viscosity of less than 1000 mPas at 20° C., and is essentially free of visual precipitates, determined in accordance with USP <790>, after storage for at least 1 months at a temperature of less than or equal to 10° C., such as 0° C.-10° C., such as 2° C.-8° C., and subsequent equilibration at room temperature for a period of at least one hour. In one aspect the glass syringe or glass cartridge, containing a lipid-based pre-formulation, wherein pre-formulations contains or consist of no more than (NMT) 6000 particles (precipitate and/or turbidity) larger than or equal to 10 μm, and/or NMT 600 particles (precipitate and/or turbidity) larger than, or equal to 25 μm as determined by USP <788>.

Viewed from a second aspect, the present disclosure provides a method of administering a lipid-based pre-formulation compressed in a glass syringe or glass cartridge according to the accompanying claims, and herein described embodiments and aspects to a patient in need thereof wherein the glass syringe or glass cartridge containing the pre-formulation is maintained at a temperature of less than or equal to 10° C., such as 0° C.-10° C., such as 2° C.-8° C. prior to administration and is allowed to equilibrate at room temperature prior to administration.

Viewed from a third aspect, the present disclosure provides the use of a diacyl glycerol composition having a fatty acid composition of at least 98% oleic acid (18:1), as determined in accordance with method C, 2.4.22 (Composition of fatty acids by gas chromatography), European Pharmacopoeia 9.0 in preventing or reducing the formation of long-lived precipitates in a pre-formulation comprising said diacyl glycerol composition and at least one biocompatible organic solvent.

Viewed from a fourth aspect, the present disclosure provides a method for preventing or reducing the formation of long-lived precipitates in a pre-formulation comprising:
  (i) a diacyl glycerol composition; and
  (ii) at least one biocompatible organic solvent;
  when said pre-formulation is stored at a temperature of 0° C. to 10° C., such as 2° C. to 8° C., for a period of at least 24 hours, such as at least 1 month, such as at least 3 months, such as at least 6 months; said method comprising forming said pre-formulation with a diacyl glycerol composition according to the first aspect. An example of the fourth aspect is a method for preventing or reducing the formation of long-lived precipitates in a lipid-based pre-formulation comprising:
  a) (i) 20-80 wt % of a diacyl glycerol having a fatty acid composition of at least 98% oleic acid (18:1), as determined in accordance with method C, 2.4.22 (Composition of fatty acids by gas chromatography), European Pharmacopoeia 9.0;
  b) 20-80 wt % of a phospholipid;
  c) 1-30 wt % of a solvent;
  d) a bioactive agent;
  when said pre-formulation is stored at a temperature of 0° C. to 10° C., such as 2° C. to 8° C., for a period of at least 24 hours, such as at least 1 month, such as at least 3 months, such as at least 6 months.

Viewed from a fifth aspect, the present disclosure provides the prefilled glass syringe or glass cartridge according to the first aspect, prefilled with a lipid-based composition, comprising a barrel having an inner surface, wherein the part of the inner surface of the barrel that is in constant contact with the lipid-based composition is substantially free of any pre-applied lubricant (i.e. free of silicone oil and any other pre-applied lubricant), where substantially free of any pre-applied lubricant is to be understood as no lubricant is added during manufacturing or post-manufacturing of the syringe, i.e. the inner surface is essentially free of lubricant, e.g. silicone oil, prior to filling said syringe with a lipid-based composition disclosed herein. Examples of suitable syringes are commercially available such as those marketed by Gerresheimer, Schott and BD (Becton, Dickinson and Company), e.g. 1 mL glass syringes, provided the inner surface is free from silicone oil, or free of lubricant.

In a further aspect, the present disclosure provides a method of administering a pre-formulation according to the present disclosure contained in a syringe free of silicone oil to a patient in need thereof wherein the syringe containing the pre-formulation is maintained at refrigerated temperature (e.g. between 2 and 8° C.) until around 1 h prior to administration (e.g. for up to 24 month prior to administration) and is allowed to equilibrate at room temperature (15-25° C., e.g. at 25 C) for around 1 hour before administration.

The pre-formulation should be a clear liquid, e.g. showing no visible cloudiness (turbidity), at the time of administration. The turbidity may be detected by visual inspection following USP<790>.

In a further aspect, the present disclosure provides a syringe according to the first aspect wherein the stability of the pre-formulation is at least six months, such as at least 12 months, such as at least 18 months stored at 2-8° C.

In a further aspect, the present disclosure provides a syringe according to the first aspect wherein the syringe is provided with a stopper Example are commercially available stoppers from BD or West suitable for the syringes described herein such as 1 mL glass syringes.

Additional aspect and embodiments are provided in the accompanying claims.

DESCRIPTION

Figure 1:
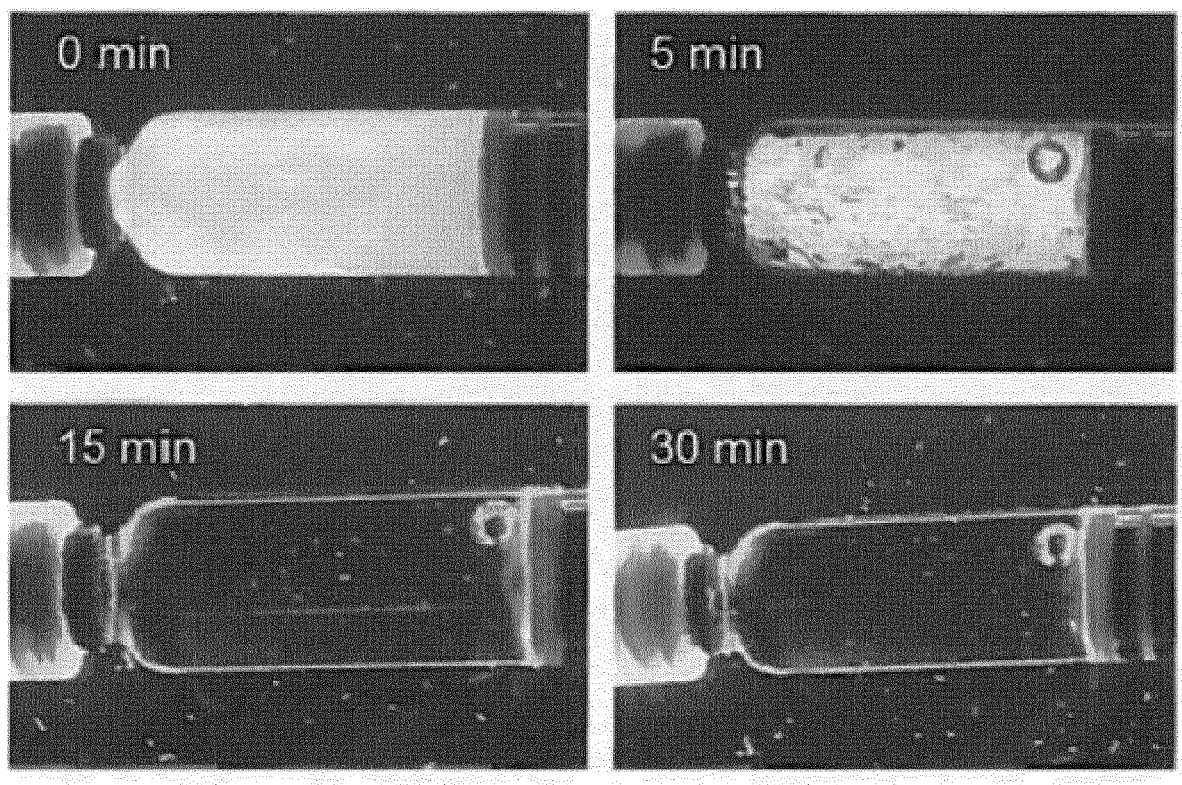
FIG. 1: Photographs, taken in polarised light, of a pre-filled syringe according to the present disclosure, stored at 5° C. for 14 months, taken 0, 5, 15, and 30 minutes after extraction from the climate chamber.

The present disclosure provides a high-purity diacyl glycerol composition. As used herein, the term "high-purity diacyl glycerol composition" is to be understood as being a composition or formulation comprising at least 97.0 wt % of a diacyl glycerol having two fatty acid residues each having 16-20 carbon atoms and one or two carbon-carbon double bonds, e.g. having a fatty acid composition of at least 98% oleic acid (18:1), as determined in accordance with method C, 2.4.22 (Composition of fatty acids by gas chromatography), European Pharmacopoeia 9.0.

All % are specified by weight herein throughout, unless otherwise indicated. Percent (%) by weight may be abbreviated e.g. as wt %. Furthermore, the % by weight indicated is the % of the total composition or formulation including all of the components indicated herein, unless otherwise indicated. Where a percentage by weight is given in relation to a salt of an active agent compound, the weight percentage relates to the amount (or equivalent amount) of free base, unless otherwise indicated. In certain Examples, the wt % of a specified salt is provided but is indicated where appropriate and may be readily converted to the corresponding weight of free base.

Where a composition or formulation is indicated as "consisting essentially of" certain components herein, the specified components provide the essential nature of that formulation, such as when the specified components constitute at least 95%, preferably at least 98%, of the formulation. This applies equally to any component or constituent which can be formed of more than one material. Similarly, where any use of "about", "around", "approximately" or similar language is present herein, this indicates that the specified amount is a primary embodiment but that the actual amount should be not materially different from that specified, as judged by the skilled worker. This will typically be ±10%, ±5% or ±1% of the value specified unless context prohibits.

Where the language "comprises or consists of" an agent or component "selected from the group consisting of", herein, particularly with reference to the claims, that language is use to indicate two embodiments; an open group for the "comprises" embodiment and a closed group for the "consists of" embodiment. In the latter case, the list of agents and components is to be considered closed and may be considered to end with "and" the final example of the list. The language may thus be read as "selected from the group consisting of . . . and . . . ".

Whenever the terms "comprising" or "containing" are used in aspects, embodiments, claims etc in the present disclosure such terms are to be understood encompassing the aspects, embodiments, and claims where said terms have be replaced by "consisting essentially of", or "consist of". Particular examples are whenever the term "a glass syringe or a glass cartridge, containing a lipid-based pre-formulation" also the following are considered explicitly contemplated "a glass syringe or a glass cartridge, consisting essentially of a lipid-based pre-formulation" as well as "a glass syringe or a glass cartridge, consisting of a lipid-based pre-formulation".

Where any active agent (e.g. drug or API) is indicated herein, this is also a disclosure of the active agent in the form of any pharmaceutically acceptable salt, unless context prohibits. Suitable pharmaceutical salts are well known in the art and suitable examples for all embodiments are described herein. Salts such as the halide (especially chloride), acetate, pamoate, etc. are examples of suitable salts of basic moieties. Alkali metal, alkaline earth metal, amine or alkyl amine salts are examples of suitable salts of acid moieties.

The term "precursor formulation" or pre-formulation is used herein to indicate the medicament formulation which may be injected to generate a controlled-release "depot" formulation within the body of the subject. The pre-formulations can optionally consist of essentially only the components indicated herein (including where appropriate additional optional components indicated herein below and in the attached claims) and in one aspect consist entirely of such components.

In one embodiment, the diacyl glycerol composition of any appropriate aspect comprises at least 97.5 wt %, such as at least 98.0 wt %, such as at least 98.5 wt %, of a diacyl glycerol having two fatty acid residues each independently having 16-20 carbon atoms and one or two carbon-carbon double bonds. In one embodiment the diacyl glycerol composition consists essentially of diacyl glycerols having two fatty acid residues each independently having 16-20 carbon atoms and one or two carbon-carbon double bonds, e.g. a glycerol dioleate having a fatty acid composition of at least 98% oleic acid (18:1), as determined in accordance with method C, 2.4.22 (Composition of fatty acids by gas chromatography), European Pharmacopoeia 9.0.

Whilst diacyl glycerol compositions are known in the prior art, diacyl glycerol compositions having a purity as high as the diacyl glycerol compositions of the present disclosure are not previously used in manufacturing pharmaceutical products, e.g. lipid-based pre-formulations, such as those described herein and used in combination with a glass syringe or glass cartridge free of pre-applied silicone lubricant (e.g. silicone oil).

The inventors have surprisingly established that when a lipid-based formulation is generated using the high purity diacyl glycerol composition of the present disclosure, instead of the conventional diacyl glycerol compositions (of lower purity) known in the prior art, the turbidity observed after thawing said lipid-based composition after it has been stored under refrigerated conditions is reduced or eliminated (e.g. determined by visual inspection according to USP <790>). The inventors have also established a method by which diacyl glycerols of high purity may be synthesized.

Without wishing to be bound by theory, it is believed that the presence of saturated impurities in the lipid-based composition is responsible for the turbidity observed when a formulation incorporating that composition is stored under refrigerated conditions and subsequently equilibrated at room temperature. By preparing the formulation with a diacyl glycerol composition having high purity, the amount of saturated impurities in the formulation may be reduced, and hence the amount of insoluble long-lived precipitates formed on refrigerated storage and subsequent thawing is also reduced.

In one embodiment therefore, the diacyl glycerol composition comprises less than 3 wt % of saturated fatty acid residues. In one embodiment, the diacyl glycerol composition comprises less than 2 wt %, such as less than 1 wt % of saturated fatty acid residues. The amount of saturated fatty acid residues in the diacyl glycerol composition can be measured by any means known in the art, such as gas chromatography (GC). A particularly suitable method can be found in Method C, 2.4.22 (Composition of fatty acids by gas chromatography), European Pharmacopoeia 9.0.

The fatty acid residues of the desired diacyl glycerols each independently have 16-20 carbon atoms. In one embodiment, the fatty acid residues of the diacyl glycerol each independently have 16-20 carbon atoms. In one embodiment, the fatty acid residues each independently have 16 or 18 carbon atoms. In one embodiment, the fatty acid residues each have 16 carbon atoms or each have 18 carbon atoms. In one embodiment the fatty acid residues each have 18 carbon atoms.

The fatty acid residues of the desired diacyl glycerols each independently have one or two carbon-carbon double bonds. In one embodiment, the fatty acid residues of the diacyl glycerol each have 1 carbon-carbon double bond or each have 2 carbon-carbon double bonds. In one embodiment, the fatty acid residues each have 1 carbon-carbon double bond.

In one embodiment, the fatty acid residues of the diacyl glycerols are independently oleic acid residues (C18:1) or linoleic acid residues (C18:2). The designation "CX:Z" indicates a hydrocarbon chain having X carbon atoms and Z unsaturations (especially double bonds). In one embodiment, the fatty acid residues are each oleate residues or each linoleate residues. In one embodiment, the fatty acid residues are each oleate residues i.e. the diacyl glycerol is glycerol dioleate. In all aspects herein, it is a key embodiment that the diacyl glycerol referred to herein may be glycerol dioleate, glycerol dilinoleate or mixtures thereof. In one embodiment, the diacyl glycerol referred to herein in all aspects may be glycerol dioleate.

In one embodiment, the diacyl glycerol having two fatty acid residues each having 16-20 carbon atoms and one or two carbon-carbon double bonds is a mixture of 1,2-diacyl glycerol and 1,3-diacyl glycerol isomers. In one embodiment the isomeric ratio of 1,2-diacyl glycerol to 1,3-diacyl glycerol is between 5:1 and 1:5, such as between 4:1 and 1:4, such as between 1:1.5 and 1:3.5 (e.g. 1:2 to 1:3).

In one embodiment, the diacyl glycerol composition comprises no more than 2 wt %, such as no more than 1.5 wt %, such as no more than 1 wt %, such as no more than 0.5 wt %, of monoacyl glycerol. In one embodiment, the diacyl glycerol composition comprises no more than 2.5 wt %, such as no more than 2 wt %, such as no more than 1.5 wt %, of triacyl glycerol.

Pre-Formulations

In one aspect the present disclosure relates to a precursor formulations (also termed "pre-formulations") comprising i) a diacyl glycerol composition having a fatty acid composition of at least 98% oleic acid (18:1), as determined in accordance with method C, 2.4.22 (Composition of fatty acids by gas chromatography), European Pharmacopoeia 9.0, and ii) at least one biocompatible organic solvent. The diacyl glycerol composition component i) may be the diacyl glycerol composition described herein.

As used herein, the terms "formulation" or "pre-formulation" relate to the mixture of components (i) and (ii), and optionally other components, The pre-formulation is typically of low viscosity. The term "pre-formulation" indicates that the formulation forms, or is capable of forming, at least one non-lamellar (especially liquid crystalline) phase structure upon contact with excess aqueous fluid.

The term "depot" relates to the composition which is formed upon exposure of the pre-formulation to excess aqueous fluid, e.g. during parenteral administration. Without wishing to be bound by theory, it is thought that this change is brought about at least in part by exchange of solvent (ii) for aqueous fluid and/or by addition of aqueous fluid to the lipid structure. The depot typically has a much higher viscosity than the corresponding pre-formulation and provides for the gradual release of any active agent contained within the depot.

In one embodiment, the pre-formulations of the present disclosure generate a non-lamellar phase (e.g. non-lamellar liquid crystalline phase) following administration. The use of non-lamellar phase structures (such as liquid crystalline phases) in the delivery of bioactive agents is now relatively well established. An effective lipid depot system is described in WO2005/117830 (which is incorporated herein by reference). For a description of the most favourable phase structures of such formulations, attention is drawn to the discussion in WO2005/117830 and particularly to page 29 thereof. Preferably the pre-formulation according to the disclosure has a molecular solution or $L_2$ phase structure prior to administration.

The pre-formulations of the disclosure form, or are capable of forming, at least one liquid crystalline phase structure upon contact with excess aqueous fluid. Herein, "excess aqueous fluid" is to be understood as a volume of aqueous fluid at least 10 times greater than the volume of pre-formulation (such as 10 to 1000 times).

In one embodiment, applicable to all aspects of the disclosure, the pre-formulations according to the disclosure have a molecular solution or $L_2$ phase structure (prior to administration). The pre-formulation forms a non-lamellar (e.g. liquid crystalline) phase following administration. Such a phase change is typically brought about by absorption of aqueous fluid from the physiological environment, as indicated herein. Although it has previously been established in WO2012/160213 that a carefully controlled amount of water can be tolerated provided that a mono-alcoholic solvent is present, it will be understood that upon administration the pre-formulation is exposed to a large amount of aqueous fluid in vivo which leads to the formation of a non-lamellar phase. Typically the pre-formulation will form a non-lamellar phase upon contact with at least an equivolume amount of aqueous fluid.

The viscosity of the pre-formulations of the present disclosure will be controllable by their formulations but will typically be within the range that can be effectively delivered by syringe or auto-injector within a tolerable period of time (e.g. less than 30 seconds). Suitable viscosities may be 10 to 1000 mPas at 25° C., such as 100 to 800 or 200 to 600 mPas at 25° C. Viscosities of 300 to 500 mPas at 25° C. may be suitable.

Component (i): Diacyl Glycerol Composition

The pre-formulations of the present disclosure comprise a diacyl glycerol composition having a fatty acid composition of at least 98% oleic acid (18:1), as determined in accordance with method C, 2.4.22 (Composition of fatty acids by gas chromatography), European Pharmacopoeia 9.0. In one embodiment, this diacyl glycerol composition is the only diacyl glycerol present in the pre-formulation i.e. the pre-formulation is substantially free of any diacyl glycerol other than the diacyl glycerol composition having a fatty acid composition of at least 98% oleic acid (18:1), as determined in accordance with method C, 2.4.22 (Composition of fatty acids by gas chromatography), European Pharmacopoeia 9.0.

The principle difference between the pre-formulations of the present disclosure and those known in the prior art are that the pre-formulations of the present disclosure comprise a high purity diacyl glycerol composition as defined herein. The inventors have surprisingly established that when a pre-formulation is prepared using the high purity diacyl glycerol composition of the present disclosure, optionally in combination with a syringe having an inner surface free from a pre-applied lubricant, the formation of long-lived precipitates in the composition after storage under refrigerated conditions, e.g. 2-8° C. is reduced and may be prevented, e.g. upon storage for one month or longer.

Without being bound by theory, it is believed that the formation of long-lived precipitates in the prior art formulations after storage under refrigerated conditions is due to the presence of saturated impurities in the lipid component. The use of the high purity diacyl glycerol composition of the present disclosure reduces the level of saturated impurities in the formulation and therefore prevents or reduces the formation of said long-lived precipitates.

Component (ii): Biocompatible Organic Solvent

Component (ii) of the pre-formulation of the disclosure is at least one biocompatible organic solvent. Component (ii) may be a single solvent or a mixture of two or more solvents. Since the pre-formulations generate, or are capable of generating, a depot composition following administration (e.g. in vivo), upon contact with excess aqueous fluid, it is desirable that these solvent(s) are tolerable to the subject and capable of mixing with the aqueous fluid, and/or diffusing or dissolving out of the pre-formulation into the aqueous fluid. Solvents having at least moderate water solubility are thus preferred. As will be described hereinafter, component ii) may include a polar co-solvent, e.g. propylene glycol.

As used herein, the term "biocompatible organic solvent" is to be understood as a solvent which is safe for use in a mammalian subject (e.g. human). Typically, the biocompatible organic solvent will have an LD50 (as calculated by oral administration in rats) of greater than 700 mg/kg, such as greater than 1000 mg/kg, especially greater than 1500 mg/kg. LD50 data for commonly used solvents is readily available in MSDS sheets.

In an embodiment, component ii) comprises or consists of at least one solvent selected from the group consisting of: alcohols, amines, amides and esters. Preferably component ii) comprises at least one mono-alcoholic solvent. Most preferably component ii) comprises ethanol, propanol, ispropanol, or mixtures thereof. It is particularly preferred the component ii) comprises or consists of ethanol. Component ii) may comprise or consist of a mono-alcoholic solvent, preferably ethanol, and a polar co-solvent. Mixtures comprising or consisting of ethanol and propylene glycol are appropriate. In an embodiment the biocompatible organic solvent is a biocompatible oxygen containing organic solvent. Examples of solvents are ethanol, propylene glycol (PG), water for injection (WFI), benzyl alcohol, dimethyl sulfoxide (DMSO), and N-methyl-2-pyrrolidone (NMP) and mixtures thereof. In some embodiments disclosed herein the solvent is ethanol, propylene glycol (PG), dimethyl sulfoxide (DMSO), and N-methyl-2-pyrrolidone (NMP) and mixtures thereof Component (ii) may comprise two or more components from the list of solvents above, particularly a mono-alcoholic solvent and a solvent selected from amides, sulphoxides or di-alcoholic solvents. Any solvent(s) which is not a mono-alcoholic solvent may be referred to herein as the co-solvent. Where two or more solvents are present, appropriate combinations include ethanol and an amide (such as ethanol and N-methylpyrrolidone (NMP)), ethanol and a sulphoxide (such as ethanol and dimethylsulfoxide (DMSO)), or ethanol and a di- or poly-alcoholic solvent (such as ethanol and propylene glycol (PG)). Ethanol and PG forms one embodiment.

A suitable combination of solvents is ethanol and PG, particularly where the ratio of ethanol to PG is 1:5 to 20:1, such as 1:1 to 10:1, such as 1.5:1 to 8:1, such as 2:1 to 5:1 (e.g. around 3:1, such as 2.8:1 to 3.2:1). In one embodiment component (ii) may be a biocompatible oxygen containing solvent, such as a solvent selected from the group consisting of ethanol, NMP, propylene glycol, benzyl alcohol, DMSO dimethyl formamide, dimethyl acetamide and mixtures thereof. Component (ii) may comprise or consist of ethanol or may comprise or consist essentially of a mixture of ethanol and PG. In one embodiment, component (ii) comprises or consists essentially of propylene glycol.

The amount of component (ii) in the pre-formulation will have a considerable effect upon several features. In particular, the viscosity and the rate (and duration) of release will alter significantly with the solvent level. The amount of solvent will thus be at least sufficient to provide a low viscosity mixture but will additionally be determined so as to provide the desired release rate. This may be determined by routine methods in view of the Examples below. Typically a level of 1 to 30%, particularly 2 to 25% solvent will provide suitable release and viscosity properties. This will preferably be 2 to 20%, preferably 5 to 15% and an amount of around 10% (e.g. 10±3%) is highly effective. These levels include any co-solvent present as part of component (ii), as mentioned above.

As indicated above, the amount of component (ii) in the pre-formulations of the disclosure will be at least sufficient to provide a low viscosity mixture (e.g. a molecular solution) of components (i) and (ii), and will be easily determined for any particular combination of components by standard methods.

The phase behaviour of any pre-formulations, compositions or mixtures may be analysed by techniques such as visual observation in combination with polarized light microscopy, X-ray scattering and diffraction techniques, nuclear magnetic resonance, and cryo-transmission electron microscopy (cryo-TEM) to look for solutions, $L_2$ or $L_3$ phases, or liquid crystalline phases or as in the case of cryoTEM, dispersed fragments of such phases. Viscosity may be measured directly by standard means. As described herein, an appropriate practical viscosity is that which can effectively be syringed and particularly sterile filtered. This will be assessed easily as indicated herein.

It is preferable that little or none of component ii) contains halogen substituted hydrocarbons since these tend to have lower biocompatibility.

Component (ii) as used herein may be a single solvent or a mixture of suitable solvents but will generally be of low viscosity. This is important because one of the key aspects of the present disclosure is that it provides pre-formulations that are of low viscosity and a primary role of a suitable solvent is to reduce this viscosity. This reduction will be a combination of the effect of the lower viscosity of the solvent and the effect of the molecular interactions between solvent and lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component (ii) (single solvent or mixture) should typically be no more than 18 mPas at 20° C. This is preferably no more than 15 mPas, more preferably no more than 10 mPas and most preferably no more than 7 mPas at 20° C.

It is described in WO2012/160213 that the addition of a polar solvent in addition to a mono-alcoholic solvent results in numerous advantages including reduced viscosity and reduced active agent burst profile. In addition to the preferred aspects described previously for component ii), in one particularly preferred embodiment component ii) comprises a mono-alcoholic solvent and a polar co-solvent. The term "polar co-solvent" as used herein defines a solvent having a dielectric constant (diel) of at least 28 at 25° C., more preferably at least 30 at 25° C. but is not water or any aqueous fluid. Highly suitable examples include propylene glycol (diel ~32), and N-methyl-2-pyrrolidone (NMP, diel ~32). The preferred levels of component ii) recited herein apply equally to mixtures of mono-alcoholic solvent and a polar co-solvent unless context permits otherwise.

Typical co-solvents will have a comparatively high dielectric constant corresponding to their high polarity. Thus, suitable co-solvents will generally have a dielectric constant of at least 28 at 25° C., more preferably at least 30 at 25° C. Highly suitable examples include water (~80), propylene glycol (~32), dimethylsulphoxide (~47) and N-methyl-2-pyrrolidone (NMP, ~32). Propylene glycol is particularly useful in connection with some active agents.

In a particularly preferred embodiment component ii) comprises, consists essentially of, or consists of a mixture of a mono-alcoholic solvent and a polar co-solvent. The polar co-solvent may in one embodiment be a di-alcoholic C3-C6 organic solvent, i.e. a C3-C6 organic solvent comprising two hydroxy groups. The di-alcoholic solvent is preferably propylene glycol. When present, a polar co-solvent is included at a level of 2 to 12 wt. % of the pre-formulation, such as 3 to 10 wt. %, especially 4 to 9 wt. %. This level is counted as part of the ranges recited above for component ii). Most preferably component ii) comprises, consists essentially of, or consists of a mixture of ethanol and propylene glycol (PG).

Where both an organic mono-alcoholic solvent and a polar co-solvent are present, e.g. ethanol and PG, the ratio of mono-alcoholic solvent to polar co-solvent solvent is preferably in the range 20:80 to 70:30, preferably 30:70 to 70:30 (w/w), more preferably 40:60 to 60:40. Approximately equal amounts of mono- and di-alcoholic components are highly appropriate.

In an especially preferred embodiment component ii) is present at a level of 1 to 30% and comprises, consists or consists essentially of a mixture of ethanol and PG, wherein the ratio of ethanol to PG (w/w) is in the range of 30:70 to 70:30, preferably 40:60 to 60:40. More preferably component ii) is present at a range of 5 to 15 wt % or 8 to 18 wt %, most preferably 8-18% wt %, and is a mixture of ethanol and PG in a ratio of 40:60 to 60:40 (w/w).

For the avoidance of doubt, even where a polar co-solvent is present in the pre-formulations of the present disclosure, the total water level will remain as described in the various embodiments herein (e.g. 0.1 to 1.0 wt %).

In some embodiments particularly appropriate combinations of solvents for component (ii) include a mono-alcoholic solvent and a co-solvent selected from the group consisting of: amides, sulphoxides or diols. An especially preferred combination is ethanol and an amide, ethanol and a sulphoxide or ethanol and a diol. Particularly preferred combinations are ethanol and propylene glycol (PG); ethanol and dimethylsulphoxide (DMSO); and ethanol and N-methyl-pyrrolidone (NMP).

When present, a suitable amount of the co-solvent will typically be greater than 1% by weight of the pre-formulation, for example 2-15%, particularly 4-12.%, especially 4-10 wt. %. The combination of a mono-alcoholic solvent and a co-solvent as component (ii) has potential advantages in the compositions of the disclosure. In particular, by inclusion of some co-solvent which is miscible with the mono-alcohol component, the slight sensation that may be caused at the injection site from the alcohol content can be substantially eliminated. Thus, in one embodiment, the ratio of mono-alcoholic component: co-solvent may be in the range 30:70 to 90:10, more preferably 50:50 to 80:20, especially 60:40 to 80:20. Approximately equal amounts of components (w/w) are highly appropriate.

Optional Phospholipid Component

In one embodiment, the pre-formulation of the disclosure comprises a phospholipid component.

In an embodiment the phospholipid component is present in an amount of 15 to 50 wt. % of the pre-formulation. In some embodiments the amount of phospholipid may be 15 to 45 wt. %, such as 20 to 45 wt. %.

In an embodiment the ratio of diacyl glycerol composition: phospholipid is 35:65 to 65:35 (w/w), such as 40:60 to 60:40, such as 45:55 to 55:45. Ratios of around 50:50 (e.g. ±2) are particularly suitable.

The phospholipid comprises a polar head group and at least one non-polar tail group. In one embodiment the phospholipid (e.g. phosphatidylcholine (PC)) will contain two non-polar groups. In particular, C12 to C20, such as C16 to C18 acyl groups, in either case having zero, one or two unsaturations (e.g. 1 or 2 unsaturations) are highly suitable as moieties forming the non-polar group of the phospholipid. In an embodiment at least 50% of the non-polar groups are oleoyl groups (C18:1).

In one embodiment, at least 50% of the non-polar groups of the phospholipid are C16 to C18 (e.g. C18:1) moieties, such as at least 75% or at least 90%. In one embodiment, approximately 100% of the non-polar groups of the phospholipid are such moieties.

In a further embodiment, at least 50% of the non-polar groups of the phospholipid are C18 (e.g. C18:1) moieties, such as at least 75% or at least 90%. In one embodiment, approximately 100% of the non-polar groups of the phospholipid are such moieties.

In an embodiment the phospholipid comprises or consists of a phospholipid which does not form a non-lamellar liquid crystalline phase structure as a pure compound in water at 25° C. In an embodiment the phospholipid comprises or consists of a phospholipid which forms a non-lamellar liquid crystalline phase structure in water at 25° C., e.g. an hexagonal liquid crystalline phase structure.

The phospholipid portion may be derived from a natural source. Suitable sources of phospholipids include egg, heart (e.g. bovine), brain, liver (e.g. bovine) and plant sources including soybean. Such sources may provide one or more constituents of the phospholipid component, which may comprise any mixture of phospholipids.

Suitable polar head groups for the phospholipid include phosphatidylcholine, phosphatidylethanolamine, phosphatidylserine and phosphatidylinositol. In one embodiment the pre-formulation comprises a phospholipid selected from the group consisting of phosphatidylcholine (PC), phosphatidylethanolamine (PE), phosphatidylserine (PS), phosphatidylinositol (PI), and mixtures thereof. It has been shown in WO2013/038460 and WO2013/083459 that the use of at least 50% PE by weight of the total amount of phospholipid can result in improved depot robustness.

In an embodiment the phospholipid comprises or consists of one or more PCs. For instance, at least 50% of the head groups of the phophospholipid should be PC, such as more that 65% of the head groups, especially more than 85% or more than 90%. A PC from a single source (e.g. soy PC), or a mixture of PCs from difference sources (e.g. soy PC and egg PC) may be used. In an embodiment the PC component contains at least 50% soy PC, such as at least 75% soy PC, or essentially pure soy PC. In an embodiment the PC component contains at least 50% egg PC, such as at least 75% egg PC, or essentially pure egg PC.

In one embodiment applicable to all aspects of the disclosure, the phospholipid comprises or consists of PC, such as PC derived from soy (soy PC). PC is available from various suppliers including Lipoid. Naturally derived PC generally comprises 18:2 fatty acids as the primary fatty acid component with 16:0 and/or 18:1 as the secondary fatty acid components. In an embodiment the ratio of between (18:2 fatty acids: other fatty acids) is 1.5:1 and 6:1. PC having approximately 60-65% 18:2, 10 to 20% 16:0, and 5-15% 18:1, with the balance predominantly other 16 carbon and 18 carbon fatty acids is particularly suitable and is typical of soy PC.

In an alternative but equally suitable embodiment, also applicable to all aspects of the disclosure, the PC component may comprise synthetic dioleoyl PC (DOPC). This is believed to provide increased stability and so will be particularly suitable for compositions needing to be stable to long term storage, and/or having a long release period in vivo. In this embodiment the PC component contains at least 50% synthetic dioleoyl PC, such as at least 75% synthetic dioleoyl PC, and may be essentially pure synthetic dioleoyl PC.

In one embodiment, the pre-formulations of the present disclosure are comprised at least partially of synthetic DOPC (i.e. PC having at least 95% PC head groups and at least 90% oleoyl (C18:1) acyl groups) and has a stability to storage at 15-25° C., defined as less than 5% active agent degradation, as assayed by HPLC, after at least 6 months, such as at least 12 months or at least 24 months.

Since the pre-formulations of the disclosure are to be administered to a subject, it is important that the components are biocompatible. In this regard, both PC and DAGs are well tolerated and are broken down in vivo into components that are naturally present in the mammalian body.

Synthetic or highly purified PCs, such as dioleoyl phosphatidylcholine (DOPC) and palmitoyl oleoyl phosphatidylcholine (POPC), as well as the other various high-purity PCs described herein, are highly appropriate as all or part of the phospholipid. As used herein, the term "highly purified" relates to PCs which are derived from a natural source by which have undergone refinement to remove contaminants. As used herein, the term "synthetic or highly purified" PC relates to material comprising at least 95 wt % phosphatidyl choline, in which the two acyl chains within PC each independently have 16 to 20 carbons, with at least one acyl chain having at least one unsaturation in the carbon chain, and no more than four unsaturations over two carbon chains.

Typically, this may be phospholipid in which at least 95% of phospholipids have a PC head group and at least 95% C16 to C20 acyl chains having 0 to 3 unsaturations.

In an embodiment the synthetic PC is DOPC (1,2-dioleoyl-sn-glycero-3-phosphocholine). In other embodiments the synthetic PC may comprise or consist of DDPC (1,2-Didecanoyl-sn-glycero-3-phosphocholine); DEPC(1,2-Dierucoyl-sn-glycero-3-phosphocholine); DLOPC(1,2-Dilinoleoyl-sn-glycero-3-phosphocholine); DLPC(1,2-Dilauroyl-sn-glycero-3-phosphocholine); DMPC(1,2-Dimyristoyl-sn-glycero-3-phosphocholine); DOPC(1,2-Dioleoyl-sn-glycero-3-phosphocholine); DPPC(1,2-Dipalmitoyl-sn-glycero-3-phosphocholine); DSPC(1,2-Distearoyl-sn-glycero-3-phosphocholine); MPPC(1-Myristoyl-2-palmitoyl-sn-glycero 3-phosphocholine); MSPC(1-Myristoyl-2-stearoyl-sn-glycero-3-phosphocholine); PMPC(1-Palmitoyl-2-myristoyl-sn-glycero-3-phosphocholine); POPC(1-Palmitoyl-2-oleoyl-sn-glycero-3-phosphocholine); PSPC(1-Palmitoyl-2-stearoyl-sn-glycero-3-phosphocholine); SMPC(1-Stearoyl-2-myristoyl-sn-glycero-3-phosphocholine); SOPC(1-Stearoyl-2-oleoyl-sn-glycero-3-phosphocholine); and SPPC(1-Stearoyl-2-palmitoyl-sn-glycero-3-phosphocholine), or any combination thereof. In all cases, synthetic PCs will preferably comprise no more than 5% (e.g. 0.01 to 5%) of other materials, such as no more than 2% or no more than 1% other materials.

Active Agent

The pre-formulations of the present disclosure comprise an active agent, also referred to as bioactive agent. The pre-formulations of the present disclosure optionally comprise one or more peptide or non-peptide active agents. It is important to note that the present disclosure is generally applicable and it is therefore envisaged that the disclosure is applicable to pre-formulations containing any bioactive agent of interest, particularly an active agent in need of refrigerated storage, or even containing no bioactive agent at all. Bioactive agents may be any compound having a desired biological or physiological effect, such as a peptide, protein, drug, antigen, nutrient, cosmetic, fragrance, flavouring, diagnostic, pharmaceutical, vitamin, or dietary agent and will be formulated at a level sufficient to provide an in vivo concentration at a functional level (including local concentrations for topical compositions). Suitable active agents include pharmaceutical agents including drugs, vaccines, and diagnostic agents. One class of active agents suitable in certain embodiments is somatostatins and somatostatin analogues, examples thereof are selected from the group consisting of SST-14, SST-28, octreotide, lanreotide, pasireotide, and vapreotide, or a salt thereof. In some aspect of the present disclosure the the bioactive agent is octreotide. In some aspect of the present disclosure the the bioactive agent is SST-14.

In one embodiment, the active agent is one that is in need of refrigeration i.e. one that would otherwise degrade if stored at room temperature for an extended period of time. As used herein, an active agent is "in need of refrigeration" if that active agent in the relevant formulation would degrade such that less than 90% of the active agent (e.g. as measured by HPLC) would remain if that active (in the formulation if appropriate) was stored at 25° C. for a period of 18 months. Examples include active agents which degrade to 90% or less of their original level when stored at 25° C. for less than 18 months, such as 12 months (e.g. 1 to 12 months), 6 months or 3 months.

In one embodiment, the active agent is one that degrades to less than 90 wt % of the original level when stored at room temperature (e.g. 25° C.) for a period of 12 months.

Examples of active agents which may be delivered by the composition of the present disclosure include, but are not limited to, antibacterial agents, immune modulating agents, including immunostimulants and immunosuppressants, anti-cancer and/or antiviral drugs such as nucleoside analogues, paclitaxel and derivatives thereof, anti-inflammatory drugs/agents, such as non-steroidal anti-inflammatory drugs and corticosteroids, cardiovascular drugs including cholesterol lowering and blood-pressure lowing agents, analgesics, anti-emetics including histamine H1, NK1 and 5-$HT_3$ receptor antagonists, corticosteroids and cannabinoids, antipsychotics and antidepressants including serotonin uptake inhibitors, prostaglandins and derivatives, vaccines, and bone modulators. Diagnostic agents include radionuclide labelled compounds and contrast agents including X-ray, ultrasound and MRI contrast enhancing agents. Nutrients include vitamins, coenzymes, dietary supplements etc.

Particularly suitable active agents include those which would normally have a short residence time in the body due to rapid breakdown or excretion and those with poor oral bioavailability, alternatively where a long duration of action would be beneficial. These include peptide, protein and nucleic acid based active agents, hormones and other naturally occurring agents in their native or modified forms. By administering such agents in the form of a depot composition formed from the composition of the present disclosure, the agents are provided at a sustained level for a length of time which may stretch to days, weeks or even several months in spite of having rapid clearance rates. This offers obvious advantages in terms of stability and patient compliance over dosing multiple times each day for the same period. In one embodiment, the active agent thus has a biological half life (upon entry into the blood stream) of less than 1 day, such as less than 12 hours, e.g. less than 6 hours. In some cases this may be as low as 1-3 hours or less. Suitable agents are also those with poor oral bioavailability relative to that achieved by injection, for where the active agent also or alternatively has a bioavailability of below 20%, such as below 2%, e.g. below 0.2%, or below 0.1% in compositions which are administered orally. Suitable active agents according to the present disclosure are those which would benefit from low temperature storage, e.g. refrigeration. Low temperature storage improves the shelf-life of the pre-formulation comprising said active agent. The pre-formulations of the invention may thus comprise an active agent "in need of refrigeration" (e.g. as described herein), may benefit from an extended shelf-life (e.g. a shelf life greater than 18 months (e.g. 24 months to 5 years) or greater than 2 years) or may contain at least one volatile component (e.g. a volatile solvent such as ethanol). Such volatile components are retained in the pre-formulation more reliably during storage if that storage takes place at refrigerated temperature.

Where technically viable, active agents disclosed herein may also be used in the form of their salts. Where "salts" of active agents are referred to here, this indicates pharmaceutically acceptable salts. Such salts are well known in the art and include, for example, chloride, acetate or pamoate salts of bases or alkali metal, alkaline earth metal, amino or alkyl amino salts of acids.

The amount of bioactive agent to be formulated with the compositions of the present disclosure will depend upon the functional dose and the period during which the depot composition formed upon administration is to provide sustained release. Typically, the dose formulated for a particular agent will be around the equivalent of the normal daily dose multiplied by the number of days the depot is to provide release. Evidently this amount will need to be tailored to take into account any adverse effects of a large dose at the beginning of treatment and so this will generally be the maximum dose used. The precise amount suitable in any case will readily be determined by suitable experimentation.

In an embodiment the composition of the disclosure may comprise one or more peptide active agents. Peptide active agents may comprise 5 to 90 or 5 to 60 natural and/or synthetic amino acids (each independently D- or L- isomers), especially 5 to 50 or 5 to 40 amino acids. In one embodiment, the active agent is a peptide active agent having no more than 45, such as no more than 30, amino acid residues. In an embodiment, the peptide active agent is a cyclic and/or constrained peptide active agent. The cyclic peptide active agent may have a ring size of 5 to 80 amino acids, e.g. 6 to 80 or 8 to 45 or 10 to 35 amino acids.

Peptide and protein based active agents include human and veterinary drugs selected from the group consisting of adrenocorticotropic hormone (ACTH) and its fragments, angiotensin and its related peptides, antibodies and their fragments, antigens and their fragments, atrial natriuretic peptides, bioadhesive peptides, bradykinins and their related peptides, calcitonin peptides including calcitonin and amylin and their related peptides, vasoactive intestinal peptides (VIP) including growth hormone releasing hormone (GHRH), glucagon, and secretin, opioid peptides including proopiomelanocortin (POMC) peptides, enkephalin pentapeptides, prodynorphin peptides and related peptides, pancreatic polypeptide-related peptides like neuropeptide (NPY), peptide YY (PYY), pancreatic polypeptide (PPY), cell surface receptor protein fragments, chemotactic peptides, cyclosporins, cytokines, dynorphins and their related peptides, endorphins and P-lidotropin fragments, enkephalin and their related proteins, enzyme inhibitors, immunostimulating peptides and polyaminoacids, fibronectin fragments and their related peptides, gastrointestinal peptides, gonadotrophin-releasing hormone (GnRH) agonists and antagonist, glucagon-like peptides 1 and 2, growth hormone releasing peptides, immunostimulating peptides, insulins and insulin-like growth factors, interleukins, luthenizing hormone releasing hormones (LHRH) and their related peptides (which are equivalent to GnRH agonists as described below), melanocortin receptor agonists and antagonists, melanocyte stimulating hormones and their related peptides, nuclear localization signal related peptides, neurotensins and their related peptides, neurotransmitter peptides, opioid peptides, oxytocins, vasopressins and their related peptides, parathyroid hormone and its fragments, protein kinases and their related peptides, somatostatins and their related peptides, substance P and its related peptides, transforming growth factors (TGF) and their related peptides, tumor necrosis factor fragments, toxins and toxoids and functional peptides such as anticancer peptides including angiostatins, antihypertension peptides, anti-blood clotting peptides, and antimicrobial peptides; selected from the group consisting of proteins such as immunoglobulins, angiogenins, bone morphogenic proteins, chemokines, colony stimulating factors (CSF), cytokines, growth factors, interferons (Type I and II), interleukins, leptins, leukaemia inhibitory factors, stem cell factors, transforming growth factors and tumor necrosis factors. An interesting class of bioactive agents suitable for the disclosure are peptide hormones, including those of the: glycoprotein hormone family (the gonadotropins (LH, FSH, hCG), thyroid stimulating hormone (TSH); proopiomelanocortin (POMC) family, adrenocorticotropic hormone (ACTH); the posterior pituitary hormones including vasopressin and oxytocin, the growth hormone family including growth hormone (GH), human chorionic somatomammotropin (hCS), prolactin (PRL), the pancreatic polypeptide family including PP, PYY and NPY; melanin-concentrating hormone, (MCH); the orexins; gastrointestinal hormones and peptides including GLP-1 and GIP; ghrelin and obestatin; adipose tissue hormones and cytokines including leptin, adiponectin, and resistin; natriuretic hormones; parathyroid hormone (PTH); the calcitonin family with calcitonin and amylin; the pancreatic hormones including insulin, glucagon and somatostatin. All synthetic peptides designed to have similar receptor affinity spectrums as the above mentioned peptides are also very suitable for the disclosure.

A further considerable advantage of the depot compositions of the present disclosure is that active agents are released gradually over long periods without the need for repeated dosing. The compositions are thus highly suitable for situations where patient compliance is difficult, unreliable or where a level dosage is highly important, such as mood-altering actives, those actives with a narrow therapeutic window, and those administered to children or to people whose lifestyle is incompatible with a reliable dosing regime and for "lifestyle" actives where the inconvenience of repeated dosing might outweigh the benefit of the active. Particular classes of actives for which this aspect offers a particular advantage include contraceptives, hormones including contraceptive hormones, and particularly hormones used in children such as growth hormone, anti-addictive agents, and drugs used in treatment of poorly compliant populations, such as patients suffering from schizophrenia, Alzheimer, or Parkinson's disease, anti-depressants and anticonvulsants Cationic peptides and proteins are particularly suitable in certain embodiments. In this embodiment, the peptide or protein may be selected from the group consisting of: octreotide, lanreotide, calcitonin, oxytocin, interferon-beta, interferon-gamma, interleukin 4, interleukin 5, interleukin 7 or interleukin 8. Other suitable cationic peptides or proteins are those having an isoelectric point above pH 7, such as above pH 8.

In one aspect a polar active agent is included in the composition. Particularly suitable polar active agents include peptide and protein actives, oligo nucleotides, and small water soluble actives, including those listed above. Of particular interest in this aspect are the peptide octreotide and other somatostatin related peptides, interferons alpha and beta, glucagon-like peptide 1 and glucagon-like peptide 2 receptor agonists, leuprorelin and other GnRH agonists, abarelix and other GnRH antagonists, granisetron and ondansetron and other 5-$HT_3$ receptor antagonists.

GnRH analogues form one particular class of active agents which may be included in pre-formulations of the present disclosure. GnRH analogues include synthetic or semi-synthetic compounds which interact with the gonadotropin-releasing hormone receptor to elicit its biological response, the release of the pituitary hormones follicle stimulating hormone (FSH) and luteinizing hormone (LH). GnRH analogues include agonists and antagonists of GnRH. Suitable GnRH analogues for use in the present disclosure include those disclosed in WO2006/075125, the disclosure of which is incorporated herein by reference. Particularly suitable GnRH analogues include those disclosed in the section from page 1 line 33 to page 2 line 29 of WO2006/075125.

Since GnRH is a peptide hormone, typical GnRH analogues will be peptides, especially of 12 or fewer amino acids. Typically, such peptides will be structurally related to GnRH I, II and/or III, and/or one or more of the known analogues, including those listed here. Peptides may contain only amino acids selected from those 20 α-amino acids indicated in the genetic code, or alternatively may contain their isomers and other natural and non-natural amino acids, (generally α, β or γ amino acids) and their analogues and derivatives. Particularly suitable GnRH analogues are constrained peptides of 6 to 12 alpha-amino acids.

In one embodiment the composition comprises a gonadotropin-releasing hormone receptor agonist selected from the group consisting of: leuprolide (aka leuprorelin), goserelin, histrelin, triptorelin, buserelin, deslorelin, and nafarelin. In one embodiment of the present disclosure the pre-formulation comprises, consists essentially of, or consists of goserelin.

Where present, the GnRH analogue will generally be formulated as 0.02 to 12% by weight of the total composition (based on the amount of free base). Typical values will be 0.1 to 10%, such as 0.2 to 8%, such as 0.5 to 6%, e.g. 1 to 5%.

Doses of the GnRH analogue suitable for inclusion in the composition, and thus the volume of composition used will depend upon the release rate (as controlled, for example by the solvent type and amount use) and release duration, as well as the desired therapeutic level, the activity of the specific agent, and the rate of clearance of the particular active chosen. Typically an amount of 0.1 to 500 mg per dose would be suitable for providing a therapeutic level for between 7 and 180 days. In an embodiment the dose of GnRH analogue in the composition may be 1 to 200 mg. For compositions comprising leuprolide or goserelin, the level will typically be around 1 to 120 mg (e.g. for a 30 to 180 day duration). Suitable amounts of leuprolide will be around 0.02 to 1 mg per day between injections for depots designed for release over 30 days to 1 year, e.g. for depots designed for release over 3 to 6 months. Evidently, the stability of the active and linearity of the release rate will mean that the loading to duration may not be a linear relationship. A depot administered every 30 days might have, for example 2 to 30 mg of GnRH analogue. A 90 day depot may have 6 to 90 mg of GnRH analogue, such as one of the GnRH analogues indicated herein.

Somatostatin and somatostatin analogues form another particular class of active agents which may be included in compositions of the present disclosure. Somatostatins (Growth Hormone Release Inhibiting Factors, SSTs) are natural peptide hormones with a wide distribution in animals, acting as neurotransmitters in the central nervous system, and having diverse paracrine/autocrine regulatory effects on several tissues. Two biologically active products are known in higher species, SST-14 and SST-28, the latter being a congener of SST-14 extended at the N-terminus. SST-14 is a 14 residue cyclic peptide hormone having a disulphide bridge to generate a type II β-turn at the key binding sequence.

Suitable somatostatins for use in the present disclosure include endogenous SST-14 and SST-18, as well as somatostatin analogues, such as those disclosed in WO2008/152401. Since SST-14 is a peptide hormone, typically somatostatin receptor agonists will be peptides, especially of 14 or fewer amino acids. Typically, such peptides will be structurally constrained such as by being cyclic and/or having at least one intra-molecular cross-link. Amide, ester or particularly disulphide crosslinks are highly suitable. In some embodiments the somatostatin analogue will exhibit a type-2 β turn. Such a turn is present in the key region of somatostatin. Peptides may contain only amino acids selected from those 20 α-amino acids indicated in the genetic code, or may contain their isomers and other natural and non-natural amino acids, (generally α, β or γ, L- or D-amino acids) and their analogues and derivatives.

Particularly suitable somatostatin analogues for use in compositions of the disclosure include those disclosed in the section from page 20 line 24 to page 21 line 19 of WO2008/152401. In some embodiments the composition may comprise an endogenous somatostatin or a somatostatin analogue selected from the group consisting of: SST-14, SST-28, octreotide, lanreotide, vapreotide, and pasireotide (aka SOM230), and salts thereof. In some the somatostatin or a somatostatin analogue is SST-14 or octreotide, and salts thereof.

When present, the somatostatin receptor agonist will generally be formulated as 0.1 to 12% by weight of the total composition (based on the amount of free base). Typical values will be 0.1 to 10%, such as 0.5 to 9%, such as 1 to 8%, e.g. 1 to 7% or 2 to 6%.

Doses of the somatostatin receptor agonist suitable for inclusion in the composition, and thus the volume of composition used, will depend upon the release rate (as controlled, for example by the solvent type and amount use) and release duration, as well as the desired therapeutic level, the activity and the rate of clearance of the particular active chosen. Typically an amount of 1 to 500 mg or 5 to 300 mg of somatostatin analogue per dose would be suitable for providing a therapeutic level for between 7 and 90 days. For octreotide, the level will typically be around 10 to 180 mg (e.g. for a 30 to 90 day duration).Typically, the amount of octreotide will be around 0.2 to 3 mg per day between injections. Thus a depot administered every 30 days would have 6 to 90 mg or a 90 day depot have 18 to 270 mg of octreotide.

For pasireotide, the dosage would typically be an amount of around 0.05 to 40 mg per week of depot duration, such as 0.1 to 20 mg per week duration (e.g. 1 to 5 mg per week) for a duration of 1 to 24 weeks, such as for a duration of 2 to 16 weeks, e.g. 3, 4, 8, 10 or 12 weeks. In an alternative embodiment the composition may be formulated for dosing weekly (e.g. every 7±1 days). A total dose of 0.05 to 250 mg of pasireotide per dose would be suitable for providing a therapeutic level for between 7 and 168 days. In some embodiments the dose of pasireotide may be 0.1 to 200 mg, such as 0.2 to 150 mg, e.g. 0.1 to 100 mg, e.g. 20 to 160 mg. Evidently, the stability of the active and effects on the release rate will mean that the loading to duration may not be a linear relationship. A depot administered every 30 days might have, for example 0.2 to 20 mg of pasireotide, or a 90 day depot might have 30 to 60 mg of pasireotide.

In another embodiment the pre-formulation comprises an active agent which is not an endogenous somatostatin or a somatostatin analogue. For example, the peptide active agent may be a peptide which does not interact as either agonist or antagonist at any of the SST(1) to SST(5) receptors (especially the corresponding human receptors).

In this alternative embodiment, such pre-formulations will not contain any somatostatin or a somatostatin analogue active agent. That is to say, an active agent is present which does not fall within the scope of somatostatin analogues described in the preceding section. In particular, in this embodiment the pre-formulation may comprise an active agent which is not selected from endogenous somatostatins, SST-14, SST-28, octreotide, lanreotide, vapreotide or pasireotide or salts thereof. Furthermore, in this embodiment endogenous somatostatins, SST-14, SST-28, octreotide, lanreotide, vapreotide or pasireotide may be entirely excluded from the pre-formulation. In one embodiment the pre-formulation is free of somatostatins, somatostatin receptor agonists and somatostatin analogues.

Other active agents which may be contained in pre-formulation of the disclosure include:
  GnRH antagonists, e.g. cetrorelix, ganirelix, abarelix, degarelix;
  GLP-1 and analogues thereof, e.g. GLP-1(7-37), GLP-1 (7-36) amide, liraglutide, semaglutide, exenatide, and lixisenatide (AVE0010);
  glucagon-like peptide 2 agonists (GLP-2) and analogues thereof, e.g. GLP-2 and elsiglutide (ZP1846);
  DPPIV inhibitors; sodium/glucose cotransporter 2 (SGLT2) inhibitors.

Other peptides suitable for the disclosure include: angiopeptin, angiotensin I, II, III, antileukinate, anti-inflammatory peptide 2, aprotinin, bradykinin, bombesin, calcitonin, calcitriol, cholecystokinin (CCK), colony-stimulating factor, corticotropin-releasing factor, C-Peptide, DDAVP, dermorphin-derived tetrapeptide (TAPS), dynorphin, endorphins, endostatin, endothelin, endothelin-1, enkephalins, epidermal growth factor, erythropoietin, fibroblast growth factor, follicle stimulating hormone, follistatin, follitropin, galanin, galanin-like peptide, galectin-1, gastrin, gastrin-releasing peptide, G-CSF, ghrelin, glial-derived neurotrophic factor, GM-CSF, granulocyte colony-stimulating factor, growth hormone, growth hormone-releasing factor, hepatocyte growth factor, insulin, insulin-like growth factors-I and I, interferons, interleukins, leptin, leukemia inhibitory factor, melanocortin 1, 2, 3, 4, melanocyte-stimulating hormone metastin, monocyte chemotactic protein-1 (MCP-1), morphiceptin, NEP1-40, neuropeptide Y, neuropeptide W, orexin-A & orexin-B, oxytocin p21-Cipl/WAF-1, TAT fusion protein, parathyroid hormone, pigment epithelium-derived growth factor (PEDF), peptide, peptide, prorenin handle region, peptide YY (3-36), platelet activating factor, platelet-derived growth factor, prorenin decapeptide, protegrin-1, PR39, prolactin, relaxin, secretin, substance P, tumor necrosis factor, urocortin, vascular endothelial growth factor, vasoactive intestinal polypeptide, vasopressin.

The short elimination half-life of opioids such as morphine, hydromorphone, and oxycodone require that these agents be administered frequently to achieve around-the-clock analgesia, which makes them excellent candidates for long acting release formulations. Fentanyl and buprenorphine undergo significant first-pass metabolism and lacks sufficient bioavailability after oral administration. Together with their high potency, fentanyl and buprenorphine are excellent candidates for the long acting injection depot compositions of the disclosure. Sufentanil, remifentanil, oxymorphone, dimorphone, dihydroetorphine, diacetylmorphine are other potent opioid receptor agonists suitable for use in the disclosure.

Buprenorphine is also used for maintenance treatment of opioid addiction as well as potentially also cocaine and amphetamine and met-amphetamine addiction, where current sublingual buprenorphine formulations suffer from low bioavailability, high variability and limited effect duration, resulting in issues with unpredictable dose response and withdrawal symptoms, particularly in mornings. These issues effectively addressed by using the injection depot compositions of the disclosure, as are problems with misuse and misdirection where the need for high sublingual doses are exploited by injection, where the effect is significantly higher for the same dose, thus facilitating misuse of the drug. Similarly, opioid antagonists can be used for treating addiction using a convenient injection depot system as provided by the disclosure. Suitable opiate antagonists for use with the disclosure are naloxone, nalmefene, and naltrexone.

Antipsychotics, including risperidone, iloperidone, paliperidone, olanzapine, asenapine, ziprazidone and aripiprazole are also highly suitable for the disclosure in view of the potential for improved treatment compliance by patients, as well as by providing stable plasma levels over time. Similarly, the disclosure is useful in the treatment of dementia, Alzheimer's disease and Parkinson's disease, which adversely affect cognition. Suitable active ingredients include donepezil, rivastigmine, galantamine, and emantine, rasagilin and pramipexol.

Another group of active agents which may be contained in pre-formulations of the disclosure are $5HT_3$ antagonists. $5HT_3$ antagonists include first and second generation $5HT_3$ antagonists. In one embodiment the pre-formulation comprises a 5HT3 antagonist selected from the group consisting of: ondansetron, tropisetron, granisetron, dolasetron, palonosetron, alosetron, cilansetron and/or ramosetron or mixtures thereof. Doses of the $5HT_3$ antagonist suitable for inclusion in the composition, and thus the volume of pre-formulation used will depend upon the release rate (as controlled, for example by the solvent type and amount use) and release duration, as well as the desired therapeutic level, the activity of the specific agent, and the rate of clearance of the particular active chosen. Typically an amount of 1 to 500 mg per dose would be suitable for providing a therapeutic level for between 5 and 90 days. Such an amount may be 1 to 300 mg per dose. For granisetron, the level will typically be around 10 to 180 mg (e.g. for a 3 to 60 day duration). Typically, the amount of granisetron will be around 0.2 to 3 mg per day between injections, for depots designed for release over 30 days to 1 year, such as for depots designed for release over 3 to 6 months. Evidently, the stability of the active and linearity of the release rate will mean that the loading to duration may not be a linear relationship. A depot administered every 30 days might have, for example 2 to 30 mg or a 90 day depot have 6 to 90 mg of active.

In an embodiment the active agent is granisetron, buprenorphine, or mixtures of granisetron and buprenorphine, and salts thereof.

In an embodiment the composition comprises at least one active agent which is not a somatostatin receptor agonist. In this embodiment the composition may be entirely free from somatostatin receptor agonists. Thus, the composition may be free of an active agent which interacts as either agonist or antagonist at any of the SST(1) to SST(5) receptors (particularly in humans).

Other Optional Components

In one embodiment the pre-formulation comprises at least 10 ppm EDTA. Suitable pre-formulations comprising e.g. an amine such as ethanolamine and EDTA are described in WO2018/060212 (especially pages 18 to 21), which complete document is incorporated herein by reference. Appropriate EDTA salts enabling the presence of EDTA in the pre-formulation include tetrakis(ethanolammonium) EDTA or EDTA salts of ethanolamine, diethanolamine, meglumine, tris-hydroxymethylamine, ethylenediamine and/or serinol.

Administration

The pre-formulations of the present disclosure are generally formulated to be administered parenterally, e.g by subcutaneous injection. This administration will generally not be an intra-vascular method but will be subcutaneous (s.c.), intracavitary or intramuscular (i.m.). Typically the administration will be by injection, which term is used herein to indicate any method in which the formulation is passed through the skin, such as by needle, catheter or needle-less (needle-free) injector.

Preferred parenteral administration is by i.m or s.c. injection, most preferably by s.c. injection. An important feature of the composition of the disclosure is that it can be administered both by i.m. and s.c. and other routes without toxicity or significant local effects. It is also suitable for intracavital administration. The deep s.c. injection has the advantage of being less deep and less painful to the subject than the (deep) i.m. injection used for some current depots and is technically most suitable in the present case as it combines ease of injection with low risk of local side effects. It is a surprising observation of the present inventors that the formulations provide sustained release of active agent over a predictable time period by both subcutaneous and intramuscular injection. This therefore allows the site of injection to be varied widely and allows the dose to be administered without detailed consideration of the tissue depth at the site of injection.

In one embodiment applicable to all aspects of the disclosure, the pre-formulations disclosed herein may be administered by means of an automatic injection device, e.g. an autoinjector which typically comprise a pre-filled glass syringe or glass cartridge (e.g. a glass syringe or cartridge) provided the inner surface is free from pre-applied silicone lubricant, a mechanical or electrical means for expelling the formulation (e.g. a spring or other elastic material under tension or compression or an electrical motor with a battery for power), a trigger or switch for initiating injection and a needle through which injection is achieved. Such an autoinjector filled with any formulation of the present disclosure will evidently form a further aspect.

The preferred lipid pre-formulations of the present disclosure provide non-lamellar liquid crystalline depot compositions upon exposure to aqueous fluids, especially in vivo. As used herein, the term "non-lamellar" is used to indicate a normal or reversed liquid crystalline phase (such as a cubic or hexagonal phase) or the $L_3$ phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise. The skilled reader will have no difficulty in identifying those compositions having appropriate phase behaviour by reference to the description and Examples provided herein, and to WO2005/117830, but the most favoured compositional area for phase behaviour is where ratio of component i): phospholipid is in the region of 40:60 to 70:30, preferably 45:55 to 55:45 and more preferably 40:60 to 54:46. Ratios of around 50:50 (e.g. ±2) are highly preferred, most preferably around 50:50.

It is important to appreciate that the pre-formulations of the present disclosure are of low viscosity (e.g. as discussed herein). As a result, these pre-formulations must not be in any bulk liquid crystalline phase since all liquid crystalline phases have a viscosity significantly higher than could be administered by syringe or similar injecting dispenser. The pre-formulations of the present disclosure will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than 5 wt %, preferably greater than 7%, and most preferably greater than 9% of organic mono-alcoholic solvent having a viscosity reducing effect. The pre-formulations of the disclosure which are in $L_2$ phase form one preferred set of pre-formulations and these will generally contain at least 2% water as polar solvent.

As used herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a small gauge needle. Preferably, the low viscosity mixtures can be dispensed through a needle of 19 gauge, preferably smaller than 19 gauge, such as 22G (22 gauge), more preferably 23 G (optionally even 25 gauge or 27 gauge or 29 gauge) needle by manual pressure. In a particularly preferred embodiment, the low viscosity mixture should be a mixture capable of passing through a standard sterile filtration membrane such as a 0.22 μm syringe filter. A typical range of suitable viscosities would be, for example, 1 to 1000 mPas at 25° C. or other viscosities discussed herein. Suitable ranges of viscosity include 200-600 mPas at 25° C. or 300-500 mPas at 25° C. Thin wall (TW), extra-thin wall (ETW) and ultra-thin wall (UTW) needles are typically used in embodiments applicable to all aspects of the present disclosure. Suitable needles include 22 G UTW and 23G TW.

It has been observed that by the addition of small amounts of low viscosity organic mono-alcoholic solvent, as indicated herein, a very significant change in viscosity can be provided. For example, the addition of only 5% solvent to a lipid mixture can reduce viscosity 100-fold and addition of 10% may reduce the viscosity up to 10,000 fold. In order to achieve this non-linear, synergistic effect in lowering viscosity it is important that a solvent of appropriately low viscosity and suitable polarity be employed. Such solvents include those described herein infra. Preferred low-viscosity mixtures include molecular solutions, including dispersions of the peptide active agent in a molecular solution of the other components.

Upon administration, the preferred lipid-based pre-formulations of the present disclosure undergo a phase structure transition from a low viscosity mixture to a high viscosity (generally tissue adherent) depot composition. Generally this will be a transition from a molecular mixture, swollen $L_2$ and/or $L_3$ phase to one or more (high viscosity) liquid crystalline phases such as normal or reversed hexagonal or cubic liquid crystalline phases or mixtures thereof. Further phase transitions may also take place following administration. Obviously, complete phase transition is not necessary for the functioning of the disclosure but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. from 1 second up to 30 minutes, preferably up to 10 minutes, more preferably 5 minutes of less). The remainder of the composition may change phase to a liquid crystalline phase more slowly by diffusion and/or as the surface region disperses.

Without being bound by theory, it is believed that upon exposure to excess aqueous fluid, the pre-formulations of the disclosure lose some or all of the organic solvent included therein (e.g. by diffusion) and take in aqueous fluid from the bodily environment (e.g. the in vivo environment). For lipid pre-formulations, at least a part of the formulation preferably generates a non-lamellar, particularly liquid crystalline phase structure. In most cases these non-lamellar structures are highly viscous and are not easily dissolved or dispersed into the in vivo environment. The result is a monolithic "depot" generated in vivo with only a limited area of exposure to body fluids. Furthermore, because the non-lamellar structure has large polar, apolar and boundary regions, the lipid depot is highly effective in solubilising and stabilising active agents such as peptides and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the disclosure are highly suitable for active agents with a relatively low biological half-life (see above).

By incorporation of at least 10% of a polar solvent (especially at least 5% water) into the pre-formulations, it is believed that the rate of phase transition to a non-lamellar (e.g. liquid crystalline) phase at the surface of the injected pre-formulation can be enhanced in comparison with compositions containing organic solvents in the substantial absence of water. The performance of the resulting depot is thus improved and further control over the release of active agent achieved.

The depot systems formed by the formulations of the present disclosure are highly effective in protecting the active agent from degradation and thus allow an extended release period. The formulations of the disclosure thus may provide in vivo depots of peptide active agents which require administration only once every 5 to 90 days preferably 5 to 60 days, more preferably 6 to 32. Evidently, a longer stable release period is desirable for patient comfort and compliance, as well as demanding less time from health professionals if the composition is not to be self-administered. Where the composition is to be self-administered, patient compliance may be aided by a weekly (e.g. every 7 days, optionally ±1 day) or monthly (e.g. every 28 or 30 days (optionally ±7 days) administration so that the need to administer is not forgotten.

A considerable advantage of the depot precursors of the present disclosure is that they are stable homogeneous phases. That is to say, they may be stored for considerable periods (preferably at least 6 months) at room or refrigerator temperature, without phase separation. As well as providing advantageous storage and facile administration, this allows for the dose of peptide active agent (e.g. Somatostatin analogue, e.g. octreotide) to be selected by reference to the species, age, sex, weight, and/or physical condition of the individual subject, by means of injecting a selected volume.

The present disclosure thus provides for methods comprising the selection of a dosing amount specific to an individual, particularly by subject weight. The means for this dose selection is the choice of administration volume.

The pre-formulations of the present disclosure are highly advantageous in that they are stable to prolonged storage in their final "administration ready" form. As a result, they may readily be supplied for administration either by health professionals or by patients or their carers, who need not be fully trained health professionals and may not have the experience or skills to make up complex preparations. This is particularly important in long-duration, slow-effecting diseases such as diabetes. The amount of lipids components in the lipid-based pre-formulation will typically be at least 40% by weight of the total formulation (e.g. 40 to 95%, such as 50 to 90% or 50 to 80%).

As used herein, the terms "long-lived precipitates" and "visual precipitates" are used to indicate insoluble precipitates (e.g. particles) in the pre-formulation (e.g. a lipid-based pre-formulation in a glass syringe or a glass cartridge) that are not re-dissolved when the pre-formulation is equilibrated at room temperature (15-25° C., e.g. 25° C.) for a period of at least 15 minutes, e.g. at least 30 minutes or at least 1 hour (e.g. 1 to 24 hours). The term "refrigerated conditions" is used to indicate temperatures from 0° C. to 10° C., such as temperatures from 2° C. to 8° C. Injectable formulations, e.g. parenteral formulations, e.g. lipid-based pre-formulations, as described herein are facing regulatory demands, and the presence of particles/precipitates in formulations for parenteral (e.g. subcutaneous administration) are regulated by agencies. The glass syringes or class cartridges described herein containing a lipid-based pre-formulation is described to be (essentially) free of visual precipitates and/or turbidity (clear liquid), which may be determined in accordance with USP <790>. Additionally, containers (syringe or cartridge) as disclosed herein containing the lipid-based pre-formulations contain not more than (NMT) 6000 particles (precipitates and/or turbidity) larger than or equal to 10 μm, and/or NMT 600 particles (precipitates and/or turbidity) larger than, or equal to 25 μm as determined by USP <788>. According to USP <788> particles are to be understood as "particulate matter in injections and parenteral infusions consists of mobile undissolved particles, other than gas bubbles, unintentionally present in the solutions", i.e. USP <788> is suitable for detection, and quantification of precipitates and/or turbidity. Throughout the present specification as well as the accompanying claims it is to be understood that USP <788> may replace or may be used in conjunction with USP<790> (The European alternative to USP <788> is Ph. Eur. 2.9.19). The testing of containers may be done using method 1 (Light Obscuration Test), and in case the such containers would be out of specification the testing may be repeated using method 2 (Microscopic Particle Count).

The term "glass syringe or glass cartridge containing the lipid-based pre-formulation is essentially free of visual precipitates" as well as the term clear is used it is to be understood as the pre-formulation is acceptable for parenteral, such as subcutaneous, injection in a subject.

Use of the Diacyl Glycerol Composition

In one aspect, the present disclosure provides the use of a diacyl glycerol composition having a fatty acid composition of at least 98% oleic acid (18:1), as determined in accordance with method C, 2.4.22 (Composition of fatty acids by gas chromatography), European Pharmacopoeia 9.0; in preventing or reducing the formation of long-lived precipitates in a pre-formulation comprising i) a diacyl glycerol composition according to the first aspect of the disclosure, and ii) at least one biocompatible organic solvent.

In one embodiment, the use relates to the use of the diacyl glycerol composition, wherein the diacyl glycerol composition according to the first aspect of the disclosure is the only diacyl glycerol present in the pre-formulation i.e. the pre-formulation is substantially free of any diacyl glycerol composition other than the diacyl glycerol composition according to the first aspect of the disclosure.

The biocompatible organic solvent component ii) is the same as component ii) of the pre-formulation according to the first aspect of the disclosure. The biocompatible organic solvent component ii) in the use of the present disclosure may therefore be the same as any of the embodiments described in relation to the biocompatible organic solvent component ii) of the pre-formulation according to the aspects of the present disclosure.

In one embodiment, the use of the diacyl glycerol composition a of the disclosure is the use in preventing or reducing the formation of long-lived precipitates in a pre-formulation when said pre-formulation is stored at a temperature of 0° C. to 10° C., such as 2° C. to 8° C., for a period of at least 24 hours, such as at least 1 month, such as at least 3 months, such as at least 6 months (e.g. 6 months to 3 years). Such "cold storage" periods and conditions are applicable to all aspects where context allows. As used herein, the terms "long-lived precipitates", "precipitate", "turbidity", "opalescence" are used to indicate change in the pre-formulation, e.g. precipitates that are not re-dissolved when the pre-formulation is equilibrated/reconditioned at room temperature (e.g. 25° C.) for a period of at least one hour (e.g. 1 to 24 hours) following cold storage. Alternative reconditioning methods are warming the pre-filled syringe by help of the body temperature (e.g. by contact with the human body such as holding the syringe in the hand) for a time sufficient to recondition, e.g. 1 to 10 minutes prior to administration, or any suitable method not causing a negative effective to the active agent and/or the lipid-based formulation. Reconditioning prior to administration (injection), often also involve turning the pre-filled syringe, comprising a lipid-based composition described herein, in the hand through an arc of around 45 to 180° 5 to 50 times (e.g. around 10 to 20 times).

In another aspect, the present disclosure provides a method for preventing or reducing the formation of long-lived precipitates in a pre-formulation comprising (i) a diacyl glycerol composition; and (ii) at least one biocompatible organic solvent; when said pre-formulation is stored at a temperature of 0° C. to 10° C., such as 2° C. to 8° C., for a period of at least 24 hours, such as at least 1 month, such as at least 3 months, such as at least 6 months (e.g. 6 months to 3 years); said method comprising forming said pre-formulation with a diacyl glycerol composition according to the first aspect of the disclosure. In particular the use described is in pre-formulation as described herein combined with a glass syringe, or a glass cartridge free of silicone lubricant.

Prefilled Glass Syringe

In one aspect, the disclosure provides a prefilled glass syringe, prefilled with a lipid-based formulation (as described in any embodiment herein), comprising a syringe barrel having an inner surface, wherein the part of the inner surface of the syringe barrel that is in constant contact with the lipid-based formulation is free of any pre-applied silicone lubricant. The inventors have surprisingly established that when a pre-filled glass syringe, prefilled with a lipid-based formulation, is prepared with the part of the inner surface of the syringe barrel that is in constant contact with the lipid-based composition substantially free of any pre-applied lubricant, the formation of long-lived precipitates in the lipid-based formulation after storage under refrigerated conditions is prevented. An alternative to a prefilled glass syringe is a prefilled glass cartridge, e.g. suitable for an autoinjector, e.g. a pen.

As used herein, the term "lipid-based formulation" means any formulation which comprises a lipid component. In one embodiment, the lipid-based formulation comprises a diacyl lipid. In one embodiment, the lipid-based formulation comprises a diacyl glycerol having a fatty acid composition of at least 98% oleic acid (18:1), as determined in accordance with method C, 2.4.22 (Composition of fatty acids by gas chromatography), European Pharmacopoeia 9.0;. In one embodiment, the lipid-based formulation forms, or is capable of forming, at least one liquid crystalline phase structure upon contact with excess aqueous fluid. In one embodiment, the lipid-based formulation is a pre-formulation according to the second aspect of the disclosure (as described in any embodiment herein).

In one embodiment, the prefilled glass syringe comprises a lipid-based formulation which comprises an active agent. In one embodiment the active agent is one that is in need of refrigeration. In one embodiment the active agent is a peptide active agent such as a peptide active agent having no more than 45, such as no more than 30, amino acid residues. In one embodiment the active agent is a cyclic and/or constrained peptide active agent. In one embodiment the active agent is a somatostatin or somatostatin analogue, such as a somatostatin or somatostatin analogue selected from the group consisting of SST-14, SST-28, octreotide, lanreotide, pasireotide, and vapreotide, or a salt thereof. In one embodiment the active agent is octreotide or a salt thereof, preferably octreotide chloride.

As used herein, a surface that is "substantially free" of any pre-applied lubricant refers to a surface that is covered to less than 1% by area of any pre-applied lubricant (e.g. 1% or 0.000%), preferably less than 0.1% by area, most preferably less than 0.01% by area.

In one embodiment, the part of the inner surface of the syringe barrel that is in constant contact with the lipid-based formulation is substantially free of any pre-applied silicone lubricant.

The prefilled glass syringe of the present disclosure has a surprisingly low break-loose force. The break-loose force is the maximum amount of force required to initiate movement of the syringe plunger opposite to the syringe barrel. It represents the force required to overcome the static friction between the syringe plunger and the syringe barrel and is therefore a measure of how easy it is to inject a composition.

In one embodiment, the prefilled glass syringe has a break-loose force of no more than 35 N, preferably no more than 30 N, preferably no more than 25 N, preferably no more than 20 N, preferably no more than 15 N, preferably no more than 10 N.

Without being bound by theory, it is believed that the lipid-based formulations provide sufficient lubrication to allow the pre-filled syringe to be operated without excessive force without the need for lubricants.

The "pre-applied lubricant" referred to herein will be any lubricant typically applied to glass syringes to allow for their smooth and tolerably low friction running. Such lubricants are well known in the art. Examples may include a petroleum-based lubricant or a silicone lubricant.

The Drug Product

As described herein there are is a need for new treatment options using prolonged release (extended release etc) drug products. An example of such a drug product is a glass syringe or glass cartridge, containing a lipid-based pre-formulation, wherein at least the inner surface of the glass syringe is in contact with the lipid-based pre-formulation and said inner surface is free of pre-applied silicone lubricant, and wherein the lipid-based pre-formulation comprises
  a) 20-80 wt % of a diacyl glycerol having a fatty acid composition of at least 98% oleic acid (18:1), as determined in accordance with method C, 2.4.22 (Composition of fatty acids by gas chromatography), European Pharmacopoeia 9.0;
  b) 20-80 wt % of a phospholipid;
  c) 1-30 wt % of a solvent;
  d) a bioactive agent (e.g. in need of storage at a temperature below 10° C.);
  wherein a) and b) is at least 94 wt % of the total lipid content of the lipid-based pre-formulation, and the lipid-based pre-formulation is a clear liquid (e.g. no cloudiness or turbidity) having a viscosity of less than 1000 mPas at 20° C. and is essentially free of visual precipitates as determined in accordance with USP <790> and/or USP <788> after storage for at least 1 months at a temperature of less than or equal to 10° C., such as 0° C.-10° C., such as 2° C.-8° C., and subsequent equilibration at room temperature for a period of at least one hour.

The different components, e.g. the glass syringe, the pre-formulations, the optional stoppers described herein, are when assemble into the drug product, i.e. a glass syringe or glass cartridge comprising a pre-formulation as described herein, enabling the long term storage of active agents for which a low temperature storage, such as above the freezing point and up to 10° C., are necessary or desired in order to achieve sufficient long term stability, e.g. at least one year or longer enabling what the individual components have not been able to achieve separately. The complexity of the lipid-based pre-formulations disclosed herein, the interplay with the glass surface, and particularly the pre-applied silicone lubricant, the injectability (e.g. injection force, break loose force etc) needed to provide a safe and efficient administration of lipid-based pre-formulations containing one or more active agents for prolonged release treatment has proven challenging, in particular in view of the need to provide liquid pre-formulations (including active agent), free of precipitate and free of turbidity and/or opalescence. The herein disclosed glass syringes or glass cartridges and various aspects and embodiments have thus in combination enabled the provision of drug product(s) suitable for refrigerated storage and providing lipid-based long-acting treatments (e.g. a long duration) including active agents in need of refrigeration.

LIST OF EMBODIMENTS

E1) A diacyl glycerol composition comprising at least 97.0 wt %, such as at least 97.5 wt %, such as at least 98.0 wt %, such as at least 98.5 wt %, of a diacyl glycerol having two fatty acid residues each independently having 16-20 carbon atoms and one or two carbon-carbon double bonds.

E2) The diacyl glycerol composition according to E1 wherein the composition comprises less than 3 wt % of saturated fatty acid residues as measured by gas chromatography (GC).

E3) The diacyl glycerol composition according to E1 comprising less than 2 wt %, such as less than 1 wt % of saturated fatty acid residues as measured by gas chromatography (GC).

E4) The diacyl glycerol composition according to E2 or E3 wherein the amount of saturated fatty acid residues in the composition is calculated according to Method C, 2.4.22 (Composition of fatty acids by gas chromatography), European Pharmacopoeia 9.0.

E5) The diacyl glycerol composition according to E1-E4 wherein the diacyl glycerol is a mixture of 1,2-diacyl glycerol and 1,3-diacyl glycerol.

E6) The diacyl glycerol composition according to E5 wherein the isomeric ratio of 1,2-diacyl glycerol to 1,3-diacyl glycerol is between 5:1 and 1:5, such as between 4:1 and 1:4, such as between 1:1.5 and 1:3.5.

E7) The diacyl glycerol composition according to E1-E6 wherein the diacyl glycerol is glycerol dioleate.

E8) The diacyl glycerol composition according to E1-E7 comprising no more than 2 wt %, such as no more than 1.5 wt %, such as no more than 1 wt %, such as no more than 0.5 wt %, of monoacyl glycerol.

E9) The diacyl glycerol composition according to E1-E8 comprising no more than 2.5 wt %, such as no more than 2 wt %, such as no more than 1.5 wt %, of triacyl glycerol.

E10) A pre-formulation comprising:
  i) a diacyl glycerol composition according to any one of the preceding claims; and
  ii) at least one biocompatible organic solvent;
  wherein the pre-formulation forms, or is capable of forming, at least one liquid crystalline phase structure upon contact with excess aqueous fluid.

E11) The pre-formulation according to E10 wherein the diacyl glycerol composition according to any of E1 to E9 is the only diacyl glycerol in the pre-formulation.

E12) The pre-formulation according to E10 or E11 wherein said at least one biocompatible organic solvent is a biocompatible oxygen containing organic solvent; such as a solvent selected from the group consisting of ethanol, N-methylpyrrolidone (NMP), propylene glycol, benzyl alcohol, DMSO, and mixtures thereof.

E13) The pre-formulation according to any of E10-E12 further comprising at least one phospholipid.

E14) The pre-formulation according to E13 wherein the at least one phospholipid is selected from the group consisting of phosphatidylcholine (PC), phosphatidylethanolamine (PE), phosphatidylserine (PS), phosphatidylinositol (PI), and mixtures thereof.

E15) The pre-formulation according to E13 or E14 wherein the at least one phospholipid comprises or consists of phosphatidylcholine.

E16) The pre-formulation according to any of E13-E15 wherein the ratio of diacyl glycerol to phospholipid is in the range of 20:80 to 80:20, such as 60:40 to 40:60.

E17) The pre-formulation according to any of E10-E16 further comprising a bioactive agent.

E18) The pre-formulation according to E17 wherein the bioactive agent is in need of refrigeration, or the bioactive agent requires refrigeration.

E19) The pre-formulation according to E17 or E18, wherein the bioactive agent is a peptide active agent such as a peptide active agent having no more than 45, such as no more than 30, amino acid residues.

E20) The pre-formulation according to E19 wherein the peptide active agent is a cyclic and/or constrained peptide active agent.

E21) The pre-formulation according to E17 to E20 wherein the bioactive agent is a somatostatin or somatostatin analogue, such as a somatostatin or somatostatin analogue selected from the group consisting of SST-14, SST-28, octreotide, lanreotide, pasireotide, and vapreotide, or a salt thereof.

E22) The pre-formulation according to E17 to E20 wherein the bioactive agent is octreotide.

E23) The pre-formulation according to E17 to E20 wherein the bioactive agent is SST-14.

E24) The pre-formulation according to E10 to E23 further comprising an alkyl ammonium salt of EDTA.

E25) Use of a diacyl glycerol composition according to any of E1-E9 in preventing or reducing the formation of long-lived precipitates in a pre-formulation comprising:
(i) a diacyl glycerol composition of any of E1-E9 and
(ii) at least one biocompatible organic solvent.

E26) The use according to E23 wherein the pre-formulation is substantially free of any diacyl glycerol composition other than the diacyl glycerol composition according to any of E1-E9.

E27) The use according to E25 or E26 for preventing or reducing the formation of long-lived precipitates in a pre-formulation when said pre-formulation is stored at a temperature of 0° C. to 10° C., such as 2° C. to 8° C., for a period of at least 24 hours, such as at least 1 month, such as at least 3 months, such as at least 6 months.

E28) The use according to E25 to E27 wherein the long-lived precipitates are not re-dissolved when the pre-formulation is equilibrated at room temperature for a period of one hour.

E29) A method for preventing or reducing the formation of long-lived precipitates in a pre-formulation comprising:
(i) a diacyl glycerol composition; and
(ii) at least one biocompatible organic solvent;
when said pre-formulation is stored at a temperature of 0° C. to 10° C., such as 2° C. to 8° C., for a period of at least 24 hours, such as at least 1 month, such as at least 3 months, such as at least 6 months; said method comprising forming said pre-formulation with a diacyl glycerol composition according to any of E1 to E9.

E30) The method according to E29 wherein said pre-formulation is formed with the diacyl glycerol composition according to any of E1 to E9 as the only diacyl glycerol in the pre-formulation.

E31) The method according to E29 or E30 wherein the long-lived precipitates are not re-dissolved when the pre-formulation is equilibrated at room temperature for a period of one hour.

E32) A prefilled container comprising a glass cylinder and a stopper wherein a volume is defined by the space bounded by the glass cylinder and the stopper and wherein said volume is at least partially filled with a pre-formulation of E10 to E24.

E33) The prefilled container of E32 which is a prefilled syringe or prefilled cartridge.

E34) A prefilled glass syringe, prefilled with a lipid-based formulation, comprising a syringe barrel having an inner surface, wherein the part of the inner surface of the syringe barrel that is in constant contact with the lipid-based formulation is substantially free of any pre-applied lubricant.

E35) The prefilled glass syringe according to E34 wherein the part of the inner surface of the syringe barrel that is in constant contact with the lipid-based formulation prior to use is substantially free of any pre-applied silicone lubricant.

E36) The prefilled glass syringe according to E34 or E35 wherein the lipid-based formulation forms, or is capable of forming, at least one liquid crystalline phase structure upon contact with excess aqueous fluid.

E37) The prefilled glass syringe according to any one of E34 to E36 wherein the lipid-based formulation comprises a diacyl lipid.

E38) The prefilled glass syringe according to any one of E34 to E37 wherein the lipid-based formulation comprises a diacyl glycerol.

E39) The prefilled glass syringe according to any one of E34 to E39 wherein the lipid-based formulation comprises a diacyl glycerol composition according to any one of E1 to E9.

E40) The prefilled glass syringe according to any one of E34 to E40 wherein the lipid-based formulation further comprises a bioactive agent.

E41) The prefilled glass syringe according to E40 wherein the bioactive agent is in need of refrigeration.

E42) The prefilled glass syringe according to E40 or E41, wherein the bioactive agent is a peptide active agent such as a peptide active agent having no more than 45, such as no more than 30, amino acid residues.

E43) The prefilled glass syringe according to E42 wherein the peptide active agent is a cyclic and/or constrained peptide active agent.

E44) The prefilled glass syringe according to E40 to E43 wherein the bioactive agent is a somatostatin or somatostatin analogue, such as a somatostatin or somatostatin analogue selected from the group consisting of SST-14, SST-28, octreotide, lanreotide, pasireotide, and vapreotide, or a salt thereof.

E45) The prefilled glass syringe according to E40 to E44 wherein the bioactive agent is octreotide or a salt thereof, preferably octreotide chloride.

E46) The prefilled glass syringe according to any one of E40 to E45 wherein the lipid-based formulation is a pre-formulation according to any one of E10 to E24.

E47) The prefilled glass syringe according to any one of E40 to E46 having a break-loose force of no more than 35 N, such as no more than 30 N, no more than 25 N, no more than 20 N, no more than 15 N, no more than 10N or no more than 5 N.

E48) The prefilled glass syringe according to any one of E40 to E46 having a break-loose force of between 5 and 25 N.

E49) The prefilled glass syringe according to any one of E40 to E48 having a glide force of no more than 35 N, such as no more than 30 N, no more than 25 N, no more than 20 N, no more than 15 N, no more than 10 N or no more than 5 N.

E50) A method of administering a pre-formulation according to any of E10 to E24 to a patient in need thereof wherein a syringe containing the pre-formulation is maintained at 2 to 8° C. until around 1 h prior to administration and is allowed to equilibrate at room temperature for around 1 hour before administration.

E51) The method of E50 wherein the pre-formulation shows no visible turbidity at the time of administration.

E52) The method of E50 or E51 wherein the syringe is warmed at body temperature (e.g. by contact with the human body such as by being held in the hand) for 1 to 10 minutes prior to administration.

E53) The method of any of E49 to E52 wherein the syringe is turned in the hand through an arc of around 45 to 180° 5 to 50 times (e.g. around 10 to 20 times) prior to administration.

E54) The method co any of E49 to E53 wherein said syringe is prefilled glass syringe of any of E34 to E48

EXAMPLES

Materials

All materials used in the Examples were obtained from commercial sources and were of pharmacopoeial grade where applicable or of the highest purity grade available. The following abbreviations are used throughout the Examples:

EtOH Ethanol (99.7% Ph. Eur)
GDO Glycerol dioleate (Cithrol GDO HP-SO-(LK) from Croda)
OCT(Cl) Octreotide hydrochloride
PG Propylene glycol (Ph. Eur)
SPC Soy phosphatidylcholine (Lipoid S100 from Lipoid)

General Procedures

Preparation of 1,3-glycerol dioleate (1,3 GDO)

1 equivalent of oleic acid (99% purity) was dissolved in dichloromethane and kept under an inert atmosphere (N2) at about 23° C. The temperature was taken to 15° C. and kept between 15 and 20° C. for 25 min when 1.5 equivalents oxalyl chloride was added dropwise. The mixture was stirred under the inert atmosphere overnight. The solvent and excess oxalyl chloride was removed and the remaining residue added to a stirred and inert (N2) dichloromethane suspension containing 0.45 equivalents of dimeric 1,3-dihydroxypropane-2-one, 0.5 eq pyridine, 0.25 equivalents DMAP. The reaction mixture was kept under 20° C. for 15 h, and thereafter the formed pyridine hydrochloride was removed by filtration and washed with dichloromethane. The combined organics were washed with 5% sodium chloride, 5% sodium carbonate, 0.1 M hydrochloric acid, and thereafter again with 5% sodium chloride. The solution was dried and evaporated to give a semi-solid which was triturated using methanol, and thereafter refrigerated overnight. The collected solids were recrystallized from isopropyl ether and methanol to give 2-oxopropane-1,3-diyl dioleate (98.5% purity HPLC).

The obtained 2-oxopropane-1,3-diyl dioleate was dissolved in 500 ml tetrahydrofuran, and 20 ml water added follow by cooling to 5° C. upon stepwise addition of sodium borohydride was maintaining the temperature around 5-10° C. The reaction was monitored by HPLC and after complete reaction the addition of sodium borohydride stopped, the solvent removed, and the residue partitioned between ethyl acetate and water. The aqueous phase re-extracted with ethyl acetate and the combined organics dried over magnesium sulfate, filtered and concentrated.

The residue was recrystallized twice from hexane to give 1,3-glycerol dioleate (98.5% purity by HPLC)

Isomerization of 1,3 GDO

The obtained 1,3-glycerol dioleate was converted to a mixture of 1,2- and 1,3-glycerol dioleate in the presence of a protic solvent by diluting 1,3-glycerol dioleate with about 75 vol % ethanol and the mixture was heated to about 70° C. for 24 hours go reach a ratio of about 1.9 (1,3-GDO/1, 2-GDO). Optionally the 1,3-glycerol dioleate was allowed to reach equilibrium during 4 days in the presence of 50% ethanol and at 40° C.

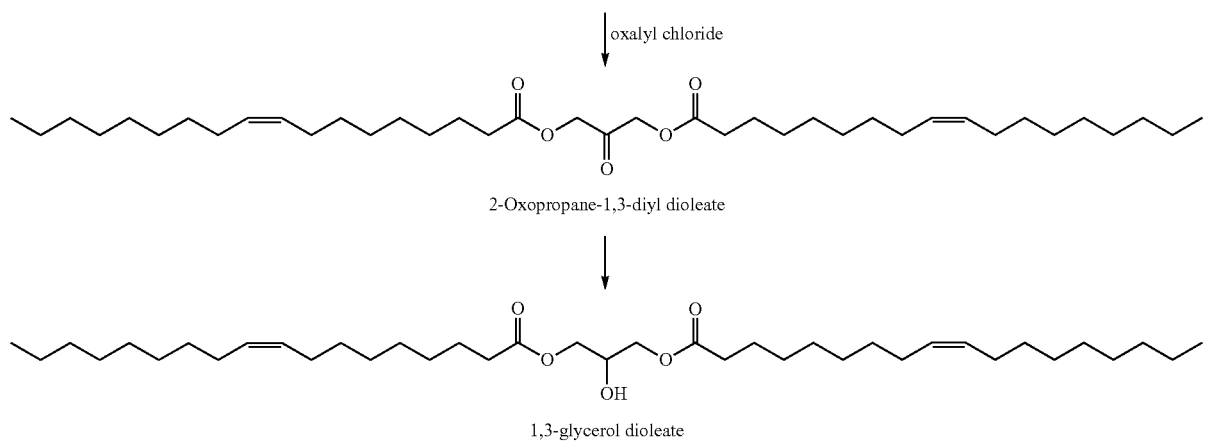

Scheme 1

The mixture of 1,2- and 1,3-glycerol dioleate obtained had a purity of 98% and not more than (NMT) 2% (area) of unsaturated fatty acids (sum of C18:2, C18:3 and C20:1), and contained NMT 1% (area) saturated fatty acids (sum of C16:0, C18:0 and C20:0) as determined according to Method C, 2.4.22. Compositions of fatty acids by GC, European Pharmacopoeia 9.0 (presented as peak area percentages of corresponding methyl ester), i.e. the fatty acid composition comprised at least 98% oleic acid (18:1).

Example 1: Storage Stability of Pre-Formulations Comprising Diacyl Glycerol Composition A lipid stock was prepared by weighing in soy phosphatidylcholine (SPC), the mixture of 1,2- and 1,3-glycerol dioleate (GDO) as prepared above, ethanol (EtOH) and propylene glycol (PG) which was left on end over end mixing until homogenous. The final formulation was prepared by adding the lipid stock to weighed octreotide chloride (OCT(Cl)) powder after which the vial was flushed with nitrogen and left on end over end mixing until homogenous. The formulation was then sterile filtered with 3 bar pressure and subsequently divided into vials and finally flushed with nitrogen. Filling of pre-filled syringes was carried out by adding about 0.5 g of formulation to each syringe using a disposable pipet under ambient air and temperature conditions. A stopper (e.g. a commercially available stopper from BD or West) was put in place with the aid of a metal wire to place the stopper into position using a plunger rod which was later detached. The gas bubble (air) in the syringes was minimized as far as possible. The syringes were then put in climate chambers and samples extracted at the specified time points for visual inspection and HPLC analysis. All syringes were pre-lubricated by silicone oil, e.g. commercially available 1 mL glass syringes such as those marketed by Gerresheimer, Schott and BD (Becton, Dickinson and Company). Comparative compositions were prepared as above with the exception that GDO from a commercial source (Cithrol GDO HP-SO-(LK) from Croda) was used instead of the disclosed GDO as prepared above.

Additionally, samples (3-10) were prepared using similar procedures but including other excipients and optionally excluding active agent (octreotide chloride) and included to Table 1.

From samples 1-10 extracts were taken at day 0, after 1, 3, 6, 12, and 14 months.

Extracts from samples stored at 15° C., 25° C./60% RH, 40° C./75% RH remained clean and homogenous throughout the test period. Extracts from samples stored at 2-8° C. were often frozen and visually inspected and inspected under polarized light. Results from the inspections of the samples stored at refrigerated conditions are presented in Table 2.

TABLE 2

| Sample No.: | Day 0 | 1 month | 3 months | 6 months | 12 months | 14 months |
|---|---|---|---|---|---|---|
| 1* | Pass | Pass | Fail | Fail | Fail | Fail |
| 2 | Pass | Pass | Pass | Pass | Pass | Pass |
| 3* | Pass | Pass | Fail | Fail | Fail | Fail |
| 4 | Pass | Pass | Pass | Pass | Pass | Pass |
| 5* | Pass | Fail | Fail | Fail | Fail | Fail |
| 6 | Pass | Fail | Fail | Fail | Fail | Fail |
| 7* | Pass | Pass | Pass | Pass | Fail | Fail |
| 8 | Pass | Pass | Pass | Pass | Pass | Pass |
| 9* | Pass | Pass | Fail | Fail | Fail | Fail |
| 10 | Pass | Pass | Pass | Pass | Pass | Pass |

*comparative

Upon inspection of the refrigerated extracts it turned out that the formulations prepared using conventional GDO contained a precipitate, once thawed, and/or the samples displayed turbidity or opalescence. The precipitates appeared to be grain-like crystals allocated near the stopper and the glass walls.

FIG. 1 shows a pre-filled syringe, prefilled with Sample No. 2, stored at 5° C. for 14 months, photographed in polarized light. The photographs are taken 0, 5, 15, and 30 minutes after extraction from the climate chamber. Note that the white spots observed in the background are not present in the formulation and that the formulation appeared completely clear within 15 min equilibration at RT.

Analysis of other samples (3-10) stored at 2-8° C. indicated the presence of precipitates which generally (but not always) re-dissolved within a couple of hours at room temperature, however in some sample amounts of precipitate, turbidity and/or opalescence remained. Some of the samples stored at 5° C., and at 15° C. indicated opalescence at the one-hour inspection upon room temperature conditioning. Opalescence were generally more pronounced in the

TABLE 1

| | Compositions (wt %) | | | | | | | |
|---|---|---|---|---|---|---|---|---|
| Sample No.: | Active agent | SPC | DOPC | GDO (comparative) | GDO** | EtOH | PG | WFI |
| 1* | 2.4 OCT(Cl) | 42.3 | — | 42.3 | — | 6.5 | 6.5 | — |
| 2 | 2.4 OCT(Cl) | 42.3 | — | — | 42.3 | 6.5 | 6.5 | — |
| 3* | — | 45 | — | 45 | — | 10 | — | — |
| 4 | — | 45 | — | — | 45 | 10 | — | — |
| 5* | — | 39 | — | 39 | — | 12 | — | 10 |
| 6 | — | 39 | — | — | 39 | 12 | — | 10 |
| 7* | — | — | 45 | 45 | — | 10 | | |
| 8 | — | — | 45 | — | 45 | 10 | | |
| 9* | — | 42.5 | — | 42.5 | — | 7.5 | 7.5 | |
| 10 | — | 42.5 | — | — | 42.5 | 7.5 | 7.5 | |

*comparative
**fatty acid composition comprising at least 98% oleic acid (18:1)
Samples were stored at refrigerated conditions at 2-8° C., 15° C., 25° C./60% RH, 40° C./75% RH.

comparative samples. Table 2 denote "fail" when the sample contained a precipitate or failed for other obvious reasons such as too much turbidity, opalescence was not considered a complete failure. Example 1 thus illustrates the use of a diacyl glycerol having a fatty acid composition of at least 98% oleic acid (18:1), as determined in accordance with method C, 2.4.22 (Composition of fatty acids by gas chromatography), European Pharmacopoeia 9.0 providing a substantial improvement upon storage under refrigerated conditions. Some samples were opalescent motivating further exploration in order to provide consistent lipid-based formulations useful for low temperature storage, such as between 2-8° C.

HPLC analysis of the extracts from sample no. 1 and 2 revealed the active agent being within specification for all samples and degradation of the active agent had been slowed by refrigeration such that more than 90% of the original content remained, indicating longer storage stability.

Example 2—Exploration of Turbidity and Opalescence

Turbidity and/or opalescence appeared in some of the samples prepared in example 1, although upon reviewing pre-formulations identical to those in Example 1, stored in glass vials under refrigerated conditions it was surprisingly noticed the pre-formulations did not display opalescence at visual inspection. Contrary to the syringes the glass vials were free from a pre-applied lubricant (silicone oil).

Conventionally glass syringes are treated with a lubricant, such as silicone oil, to enable acceptable injection force allowing e.g. self-administration and assuring auto-injector compatibility (e.g. taking time of injection into consideration). In order to develop an acceptable lipid-based formulation suitable for storage under refrigerated conditions further investigations were done.

The following pre-formulations without active agents were prepared as described in Example 1, and about 0.2 mL filled into 1 mL glass syringes free from pre-applied silicone oil. The syringes were sealed with a plunger, such as suitable plungers marketed by BD or West.

TABLE 3

| Sample No.: | Active agent | SPC | DOPC | GDO[1] | GDO[2] | EtOH | PG | EDTA[3] | EDTA[4] | ETA |
|---|---|---|---|---|---|---|---|---|---|---|
| 11 | — | 43.8 | — | 43.8 | — | 10.5 | — | 2.0 | — | — |
| 12* | — | 43.8 | — | 43.8 | — | 10.5 | — | 2.0 | — | — |
| 13 | — | 43.8 | — | — | 43.8 | 10.5 | — | 2.0 | — | — |
| 14* | — | 43.8 | — | — | 43.8 | 10.5 | — | 2.0 | — | — |
| 15 | — | 45.0 | — | 45.0 | — | 10.0 | — | — | 0.01 | 0.008 |
| 16* | — | 45.0 | — | 45.0 | — | 10.0 | — | — | 0.01 | 0.008 |
| 17 | — | 44.9 | — | 44.9 | — | 10.0 | — | — | 0.1 | 0.08 |
| 18* | — | 44.9 | — | 44.9 | — | 10.0 | — | — | 0.1 | 0.08 |
| 19 | — | 45.0 | — | — | 45.0 | 10.0 | — | — | 0.01 | 0.008 |
| 20* | — | 45.0 | — | — | 45.0 | 10.0 | — | — | 0.01 | 0.008 |
| 21 | — | 44.9 | — | — | 44.9 | 10.0 | — | — | 0.1 | 0.08 |
| 22* | — | 44.9 | — | — | 44.9 | 10.0 | — | — | 0.1 | 0.08 |
| 23 | — | — | 45.0 | 45.0 | — | 10.0 | — | — | 0.01 | 0.008 |
| 24* | — | — | 45.0 | 45.0 | — | 10.0 | — | — | 0.01 | 0.008 |
| 25 | — | — | 44.9 | 44.9 | — | 10.0 | — | — | 0.1 | 0.08 |
| 26* | — | — | 44.9 | 44.9 | — | 10.0 | — | — | 0.1 | 0.08 |
| 27 | — | — | 45.0 | — | 45.0 | 10.0 | — | — | 0.01 | 0.008 |
| 28* | — | — | 45.0 | — | 45.0 | 10.0 | — | — | 0.01 | 0.008 |
| 29 | — | — | 44.9 | — | 44.9 | 10.0 | — | — | 0.1 | 0.08 |
| 30* | — | — | 44.9 | — | 44.9 | 10.0 | — | — | 0.1 | 0.08 |
| 31 | — | 42.5 | — | 42.5 | — | 7.5 | 7.5 | — | 0.01 | 0.008 |
| 32* | — | 42.5 | — | 42.5 | — | 7.5 | 7.5 | — | 0.01 | 0.008 |
| 33 | — | 42.4 | — | 42.4 | — | 7.5 | 7.5 | — | 0.1 | 0.08 |
| 34* | — | 42.4 | — | 42.4 | — | 7.5 | 7.5 | — | 0.1 | 0.08 |
| 35 | — | 42.5 | — | — | 42.5 | 7.5 | 7.5 | — | 0.01 | 0.008 |
| 36* | — | 42.5 | — | — | 42.5 | 7.5 | 7.5 | — | 0.01 | 0.008 |
| 37 | — | 42.4 | — | — | 42.4 | 7.5 | 7.5 | — | 0.1 | 0.08 |
| 38* | — | 42.4 | — | — | 42.4 | 7.5 | 7.5 | — | 0.1 | 0.08 |

*conventional pre-lubricated glass syringe (silicone oil)

[1]comparative

[2]fatty acid composition comprising at least 98% oleic acid (18:1)

[3]Citric acid buffer containing 0.5 mg/mL EDTA sodium salt

[4]essentially water free systems wherein EDTA is solubilized in the lipid system by using ethanolamine (ETA), e.g. as described in WO2018/060213

Figure 4:
FIGS. 4 and 5: Photographs of pre-filled glass syringes according to Example 2.
Figure 5:

The samples were visually evaluated as described in Example 1, and for example samples 11-14 stored at 2-8° C. for 16 months and thereafter visually inspected and results presented in Table 4, and in FIGS. 4 and 5.

TABLE 4

| Sample No.: | Physical form at 5° C. | Observation 1 | Observation 2 | Observation 3 | Observation 4 | Observation 5 |
| --- | --- | --- | --- | --- | --- | --- |
| 11 | solid | 15-30 min: Liquid. Turbidity | 2 h: Small particles (FIG. 4 left) | 7 h: Opalescent sample containing precipitate, | 24 h: Opalescent sample containing precipitate | 96 h: Opalescent sample containing precipitate |
| 12 | solid | 15-30 min: Liquid. precipitate | 2 h: Clear sample containing precipitate (FIG. 4 right) | 7 h: Clear sample containing precipitate | 24 h: Clear sample containing precipitate | 96 h: Clear sample containing precipitate |
| 13 | Solid | 15-30 min: liquid, Clear and homogenous | 2 h: Clear and homogenous (FIG. 5 right) | 7 h: Clear and homogenous | 24 h: Clear and homogenous | 96 h: Clear and homogenous |
| 14 | Solid | 15-30 min: Liquid. Opalescent. | 2 h: Opalescent. (FIG. 5 left) | 15-30 min: Liquid. Opalescent. | 2 h: Opalescent. (FIG. 5 left) | 15-30 min: Liquid. Opalescent. |

Samples 11 and 12 contained precipitate and unacceptable. Sample 13 was already at the first observation consider acceptable for administration whereas sample 14 still showed opalescence throughout the evaluation.

Example 3—Determination of Force Needed for Injection

Typical injection devices deliver a force up to around 20-25 N. In order to determine a suitable configuration of formulation, needle, volume, injection mechanism and injection time, studies may be carried out using appropriate samples. Methods based upon ISO 11040 are appropriate. Needle characterization is done in accordance with ISO 9626:2016.

A pre-filled syringe containing 1 ml of lipid controlled-release formulation (placebo or containing active agent) without silicone lubricant (unsiliconized) is placed in a material tester having a 100 N load cell. The plunger rod is mounted without moving the plunger stopper (lubricated) to avoid compromising the "break-loose force" measurement. After removal of the needle cover, the test is run at a speed chosen to provide delivery of the correct dose in a specified period. The necessary load is measured over time until the plunger stopper comes into contact with the shoulder of the syringe barrel, at which point the test is halted. Break-loose force is determined using the maximum force in the force chart in the travel range of 0 mm to ≤5 mm and the glide-force is calculated from the average force between the end of the break-loose period until just before the end of the plunger travel, alternatively the maximum force from just after the end of the break-loose period until just before the end of the plunger travel is used to calculate the glide force.

The testing of lipid controlled release formulations revealed that such formulations adhere closely to the established Hagen-Poiseuille theory. In this theory, injection time is linearly dependent upon viscosity, needle length and fill volume; injection time is dependent upon the fourth power of the internal syringe (barrel) diameter and is inversely dependent on the residual force and on the internal diameter of the needle to the fourth power.

Since the formulations adhere well to the Hagen-Poiseuille theory, delivery average forces (glide force) required for various viscosities, delivery times and needle diameters can be calculated, and a model developed. Examples based on the developed model are shown in the table below.

| Estimated Glide force | Viscosity at 25° C. | Vol | Needle | Time |
| --- | --- | --- | --- | --- |
| 9N | 400 | 1 ml | 22G ultra-thin wall | 15 s |
| 20N | 300 | 1 ml | 23G thin wall | 15 s |
| 20N | 900 | 1 ml | 22G ultra-thin wall | 15 s |
| 27N | 400 | 1 ml | 23G thin wall | 15 s |

Figure 2A:
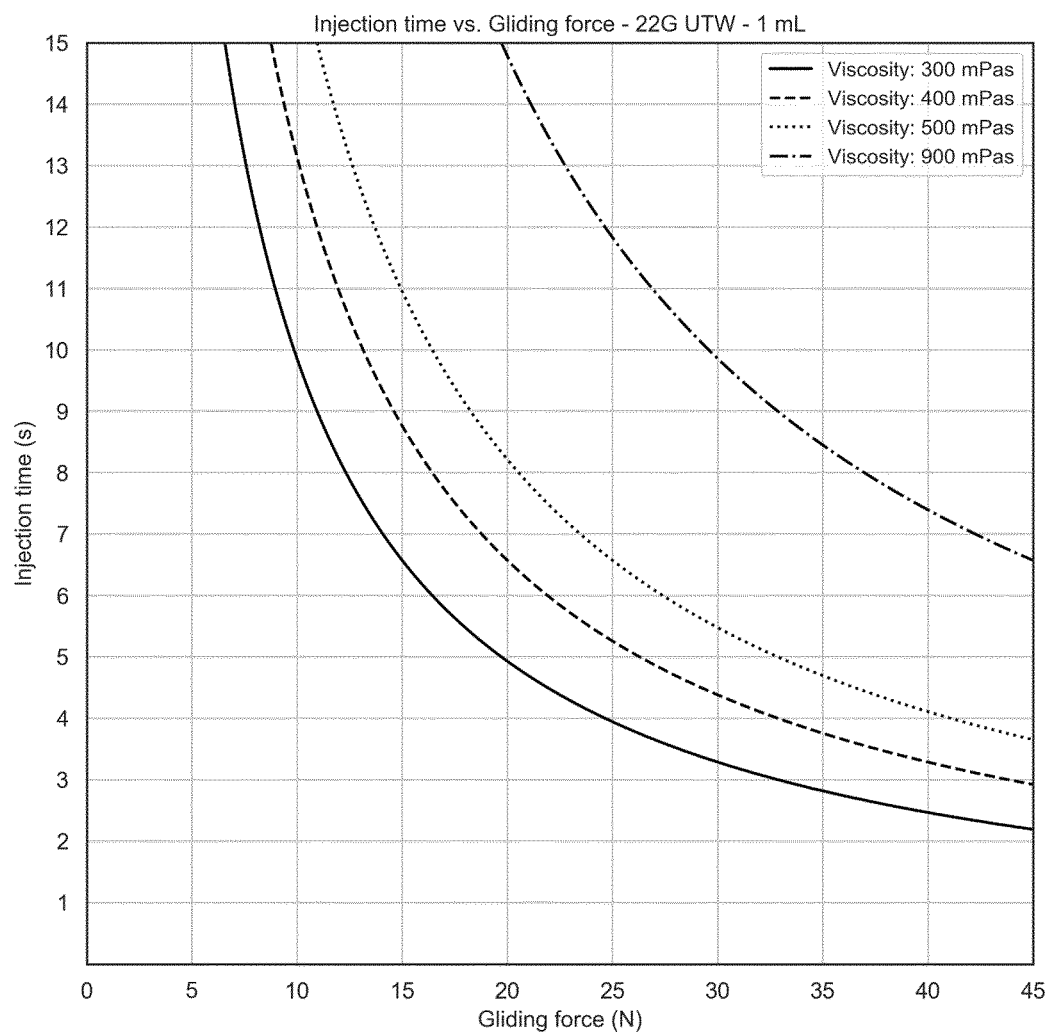
FIGS. 2a and 2b show graphs of injection time against gliding force for formulations of various viscosity injected through 22 G TW and 23 G UTW needles respectively.
Figure 2B:
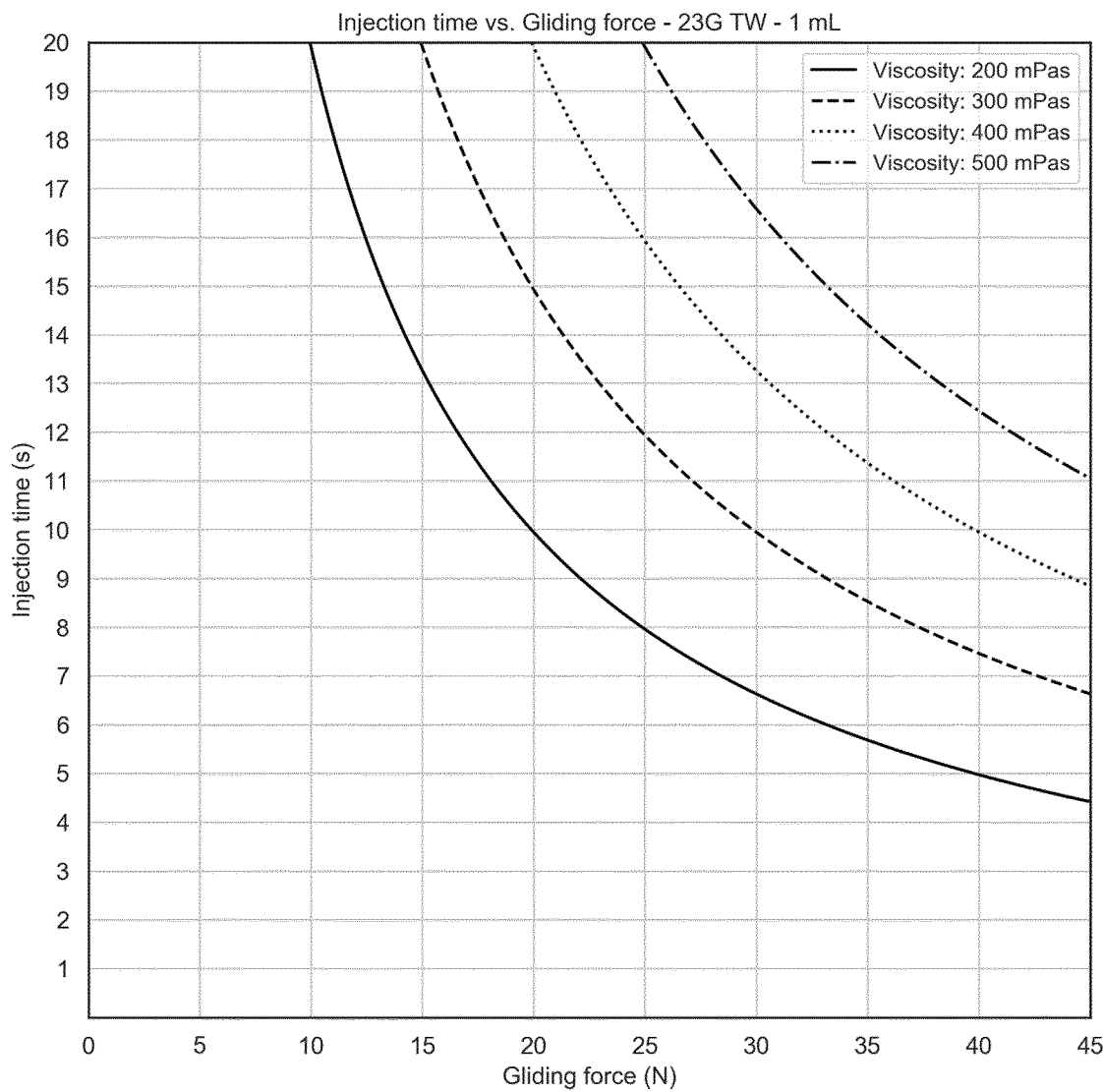

The variation of injection time with gliding force for various viscosities in the range 100 to 1000 mPas is shown in FIG. 2a (22G ultra-thin wall) and FIG. 2b (23G thin wall).

Figure 3:
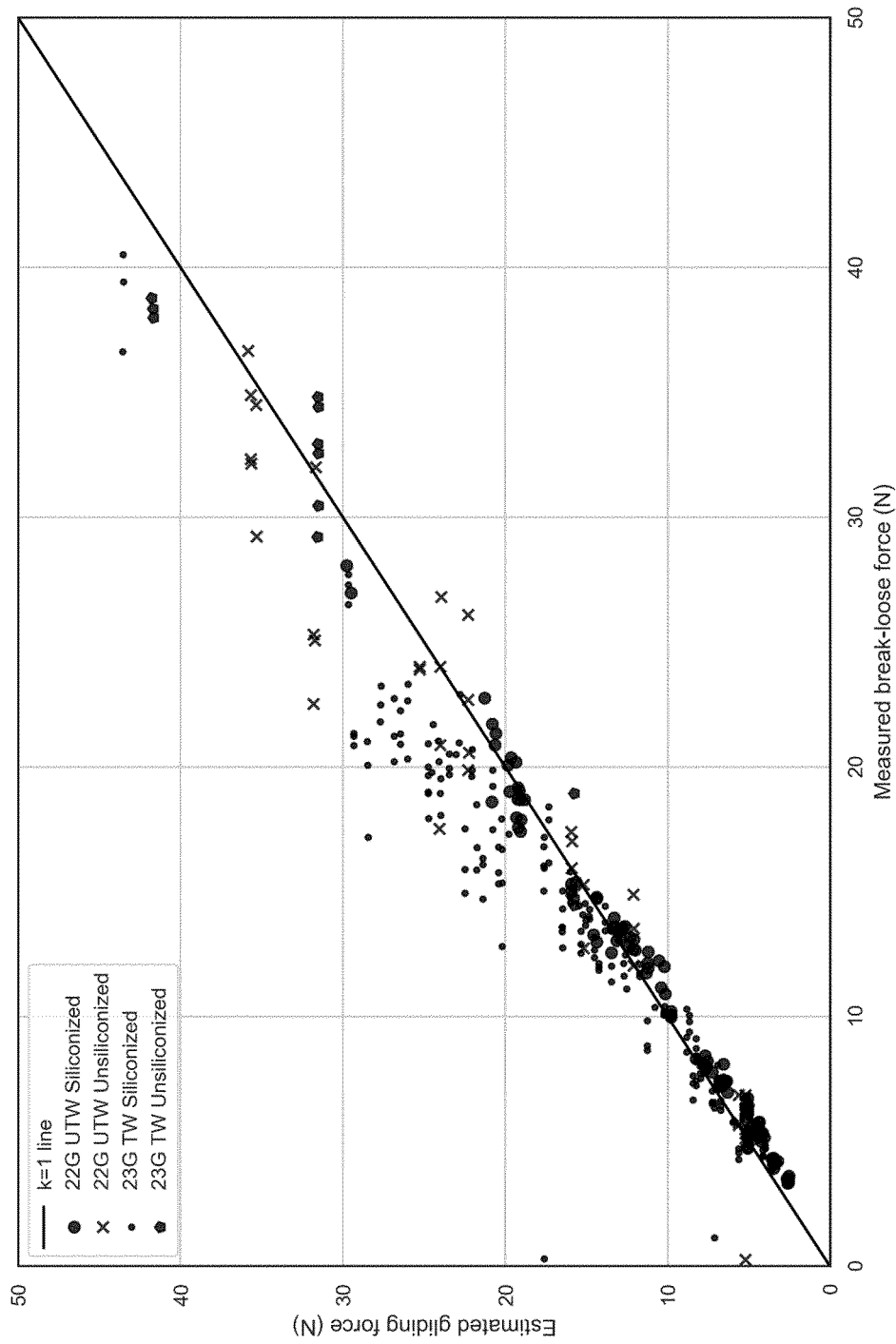
FIG. 3 shows the correlation between estimated glide force and break loose force.

The break loose force was defined as the maximum force in the range 0 mm to ≤5 mm movement of the plunger stopper inside the syringe barrel. The break loose force for the above mentioned pre-filled syringe containing 1 ml of lipid controlled-release formulation resulted in break loose forces adhering well to the estimated glide force, i.e. as disclosed in FIG. 3, and deemed suitable for self-administration or for use in an auto-injector A comparative test was conducted with corresponding empty syringes lacking silicone lubricant. The test was stopped because a force of 45 N was insufficient to provide the break loose force and glide force sufficient to inject into air (i.e. the syringe plunger did not travel the required distance) required. No greater force was applied due to the risk of shattering the glass syringe. The break loose force may be analyzed in accordance with ISO11040-4:2015 (glass barrels for injectables).

A similar test was conducted using an unsiliconized syringe with a barrel containing water, equipped with a 22 G UTW needle and an un-lubricated stopper. The force of 45 N was reached without achieving a complete injection into air.

The test was repeated using an unsiliconized syringe barrel filled with water, using a 22 G UTW needle and a silicone-lubricated stopper. The results demonstrate that injection into air with an unsiliconized barrel but a siliconized stopper is possible but high forces are required. Break loose forces around 13, 20 and 18 N respectively (plunger travel of 0.5, 1 and 5 mm/s) were obtained, and given the low viscosity of water these values are considered high.

Filling a non-lubricated syringe with a lipid composition disclosed herein did fulfill requirements of break loose as well as glide force. Thus a syringe free of lubricating silicone oil filled with a lipid composition as disclosed herein, sealed with a plunger stopper, preferably lubricated, was found to enable storage at 2-8° C. for an extended period of time without the occurrence of visible precipitates and/or turbidity such as opalescence after reconditioning at room temperature. Additionally such pre-filled syringe did not require excessive injection force, in order to inject the dedicated amount of the lipid compositions, e.g. 0.1-3 ml, over an acceptable period of time such as 3-25 s, such as 5-20 s, such as 5-15 s. Example of force needed to allow the plunger to inject the formulation is 5-25 N, such as 8-20 n. Pre-filled syringes described herein did meet the overall objective enabling low temperature storage of syringes containing active agents requiring such low temperature storage (e.g. 2-8° C.) whereas injectability and product conformity (no precipitate, and clear liquids) were enabled by aspects and embodiments described herein.

The invention claimed is:

1. A glass syringe or a glass cartridge, comprising:
an inner surface containing a lipid-based pre-formulation having a total lipid content, wherein at least the inner surface of the glass syringe or glass cartridge is in contact with the lipid-based pre-formulation and said inner surface is free of pre-applied silicone lubricant, and wherein the lipid-based pre-formulation comprises
a) 20-80 wt % of a diacyl glycerol having a fatty acid composition of at least 98% oleic acid (18:1);
b) 20-80 wt % of a phospholipid;
c) 1-30 wt % of a solvent; and
d) a bioactive agent;
wherein a) and b) are collectively at least 94 wt % of the total lipid content of the lipid-based pre-formulation, and the lipid-based pre-formulation is a clear liquid having a viscosity of less than 1000 mPas at 20° C., and is essentially free of visual precipitates after storage for at least 1 month at a temperature of less than or equal to 10° C., and subsequent equilibration at room temperature for a period of at least one hour.

2. The glass syringe or glass cartridge according to claim 1, containing no more than (NMT) 6000 particles larger than or equal to 10 μm, and/or NMT 600 particles larger than or equal to 25 μm.

3. The glass syringe or glass cartridge according to claim 1, wherein the diacyl glycerol comprises no more than 2 wt % of monoacyl glycerol.

4. The glass syringe or glass cartridge according to claim 1, wherein the pre-formulation comprises no more than 5 wt % of triacyl glycerol.

5. The glass syringe or glass cartridge according to claim 1, wherein the phospholipid is phosphatidylcholine (PC), phosphatidylethanolamine (PE), phosphatidylserine (PS), phosphatidylinositol (PI), dioleyl phosphatidylcholine, and mixtures thereof.

6. The glass syringe or glass cartridge according to claim 1, wherein the phospholipid is phosphatidylcholine (PC) or dioleyl phosphatidylcholine.

7. The glass syringe or glass cartridge according to claim 1, wherein a) and b) is at least 95 wt % of the total lipid content of the pre-formulation.

8. The glass syringe or glass cartridge according to claim 1, wherein the solvent is selected from the group consisting of ethanol, propylene glycol (PG), water for injection (WFI), benzyl alcohol, dimethyl sulfoxide (DMSO), N-methyl-2-pyrrolidone (NMP), and mixtures thereof.

9. The glass syringe or glass cartridge according to claim 1, wherein the solvent is ethanol or a mixture of ethanol and propylene glycol (PG).

10. The glass syringe or glass cartridge according to claim 1, wherein the bioactive agent is an agent in need of storage at a temperature below 10° C.

11. The glass syringe or glass cartridge according to claim 1, wherein the bioactive agent is a peptide active agent.

12. The glass syringe or glass cartridge according to claim 1, wherein the bioactive agent is a cyclic and/or constrained peptide active agent.

13. The glass syringe or glass cartridge according to claim 1, wherein at least the inner surface of the glass syringe or glass cartridge is free of pre-applied lubricant.

14. The glass syringe or glass cartridge according to claim 1, stored at least 1 month.

15. The glass syringe or glass cartridge according to claim 1, is free of visual precipitates and/or turbidity after equilibration at room temperature for a period of one hour.

16. The glass syringe or glass cartridge according to claim 1, containing 0.1 to 3 ml of the lipid-based pre-formulation.

17. The glass syringe or glass cartridge, according to claim 1, wherein a plunger sealing the syringe or cartridge has a break-loose force of no more than 35N.

18. The glass syringe or glass cartridge, according to claim 1, wherein a plunger sealing the syringe or cartridge has a glide force of no more than 35N.

19. A method comprising administering a lipid-based pre-formulation comprised in a glass syringe or glass cartridge according to claim 1 to a patient in need thereof, including maintaining the glass syringe or glass cartridge containing the pre-formulation at 2 to 8° C. prior to administration and allowing the pre-formulation to equilibrate at room temperature prior to administration.

20. The method of claim 19 wherein the pre-formulation is free from visible precipitates and/or turbidity at the time of administration.

21. The method of claim 19, wherein the syringe is warmed at body temperature for 1 to 10 minutes prior to administration, or equilibrated at room temperature for about 1 hour prior to administration.

22. The method of claim 19, further comprising turning the syringe in hand 5 to 50 times prior to administration.

23. The method of claim 22, wherein the turning the syringe in hand comprises turning the syringe in the hand through an arc of around 45 to 180°.

* * * * *